US012676733B2

(12) United States Patent
Barreras et al.

(10) Patent No.: US 12,676,733 B2
(45) Date of Patent: Jul. 7, 2026

(54) WIRELESS COMMUNICATION SECURITY FOR ANALYTE MONITORING SYSTEMS

(71) Applicant: Dexcom, Inc., San Diego, CA (US)

(72) Inventors: Jorge R. Barreras, Dania Beach, FL (US); Reinier Sanchez Bao, Boston, MA (US); Ariel Alvarez, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 210 days.

(21) Appl. No.: 18/438,271

(22) Filed: Feb. 9, 2024

(65) Prior Publication Data

US 2024/0275582 A1    Aug. 15, 2024

Related U.S. Application Data

(60) Provisional application No. 63/484,705, filed on Feb. 13, 2023.

(51) Int. Cl.
| | |
|---|---|
| *H04L 9/08* | (2006.01) |
| *A61B 5/00* | (2006.01) |
| *A61B 5/145* | (2006.01) |
| *H04L 9/30* | (2006.01) |

(52) U.S. Cl.
CPC ........ *H04L 9/0825* (2013.01); *A61B 5/14546* (2013.01); *A61B 5/742* (2013.01); *H04L 9/0863* (2013.01); *H04L 9/3066* (2013.01)

(58) Field of Classification Search
CPC ... H04L 9/0825; H04L 9/0863; H04L 9/3066; H04L 67/12; H04L 9/0841; H04L 63/168; H04L 2209/805; H04L 2209/88; H04L 9/0844; H04L 9/3271; H04L 63/0428; H04L 63/061; A61B 5/14546; A61B 5/742; H04W 4/38; H04W 12/0471; H04W 4/80; H04W 12/033
See application file for complete search history.

(56) References Cited

U.S. PATENT DOCUMENTS

| | | | |
|---|---|---|---|
| 2021/0350918 A1* | 11/2021 | Paul | .................... H04W 12/041 |
| 2022/0070666 A1 | 3/2022 | Hua et al. | |
| 2022/0150308 A1* | 5/2022 | Hua | ........................ H04W 4/80 |

* cited by examiner

*Primary Examiner* — Izunna Okeke

(74) *Attorney, Agent, or Firm* — Klarquist Sparkman, LLP

(57) ABSTRACT

Techniques for performing application-layer security are disclosed. In certain embodiments, analyte data may be obtained from an analyte sensor operatively coupled to a sensor electronics module of an analyte sensor system. Thereafter, the analyte data may be encrypted, in an application layer of a protocol stack of the sensor electronics module using a session key established between the analyte sensor system and a display device. The encrypted analyte data may then be transmitted to a display device.

20 Claims, 13 Drawing Sheets

OBTAIN INFORMATION FROM DISPLAY DEVICE

1004

PERMIT NON-ALE
COMMUNICATION?

YES

NO

1006

SET UP CONNECTION AND
COMMUNICATE WITH
DISPLAY DEVICE USING
NON-ALE COMMUNICATION
MODE

1008

SET UP CONNECTION AND
COMMUNICATE WITH
DISPLAY DEVICE USING ALE
COMMUNICATION MODE

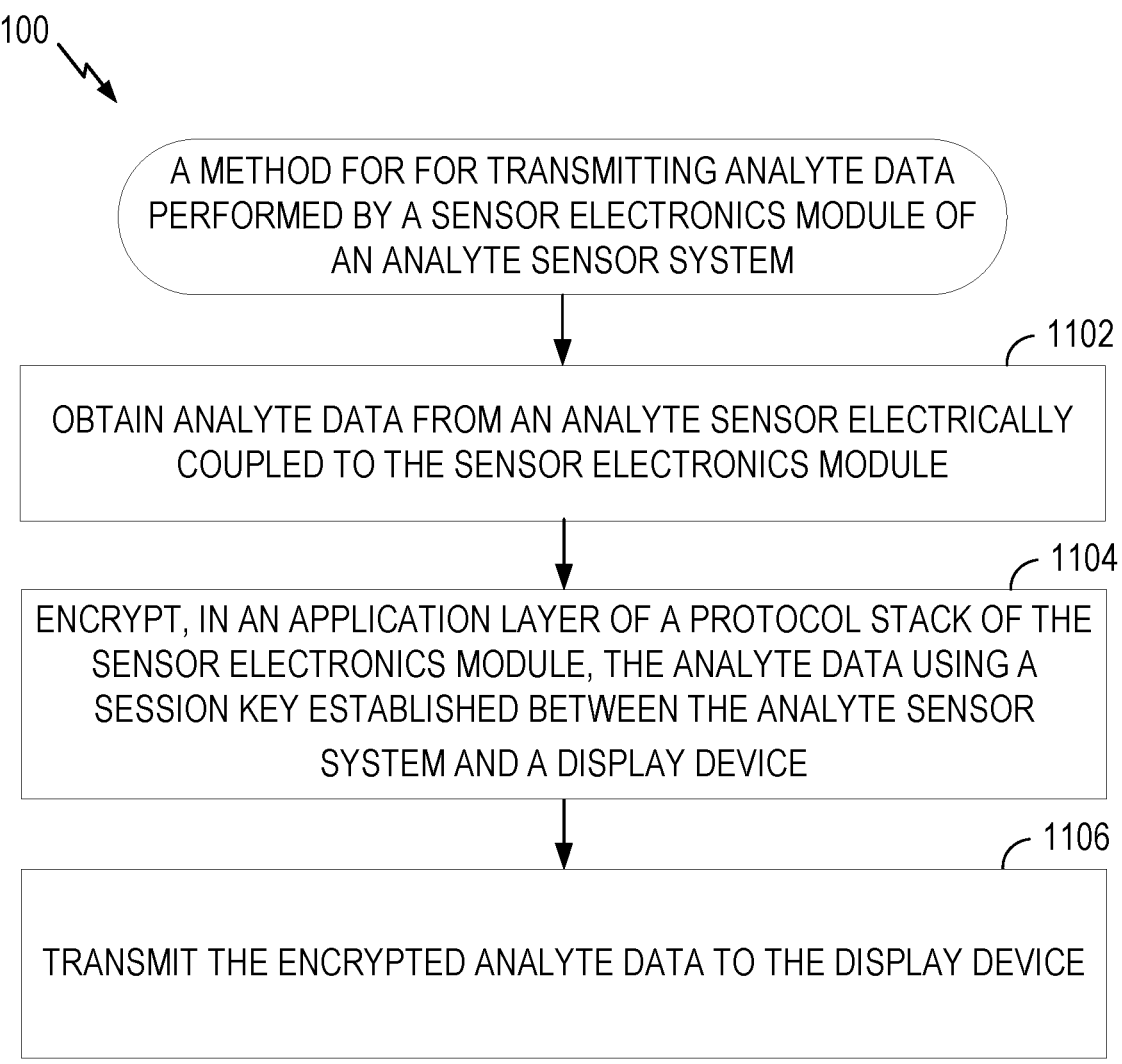

1100

A METHOD FOR FOR TRANSMITTING ANALYTE DATA PERFORMED BY A SENSOR ELECTRONICS MODULE OF AN ANALYTE SENSOR SYSTEM

1102

OBTAIN ANALYTE DATA FROM AN ANALYTE SENSOR ELECTRICALLY COUPLED TO THE SENSOR ELECTRONICS MODULE

1104

ENCRYPT, IN AN APPLICATION LAYER OF A PROTOCOL STACK OF THE SENSOR ELECTRONICS MODULE, THE ANALYTE DATA USING A SESSION KEY ESTABLISHED BETWEEN THE ANALYTE SENSOR SYSTEM AND A DISPLAY DEVICE

1106

TRANSMIT THE ENCRYPTED ANALYTE DATA TO THE DISPLAY DEVICE

A METHOD FOR FOR RECEIVING ANALYTE DATA PERFORMED BY A DISPLAY DEVICE

1202

RECEIVE ENCRYPTED ANALYTE DATA FROM AN ANALYTE SENSOR SYSTEM

1204

DECRYPT, IN AN APPLICATION LAYER OF A PROTOCOL STACK OF THE DISPLAY DEVICE, THE ANALYTE DATA USING A SESSION KEY ESTABLISHED BETWEEN THE ANALYTE SENSOR SYSTEM AND THE DISPLAY DEVICE

WIRELESS COMMUNICATION SECURITY FOR ANALYTE MONITORING SYSTEMS

CROSS-REFERENCE TO RELATED APPLICATIONS

This application claims benefit of and priority to U.S. Provisional Application No. 63/484,705, filed Feb. 13, 2023, which is hereby assigned to the assignee hereof and hereby expressly incorporated by reference herein in its entirety as if fully set forth below and for all applicable purposes.

BACKGROUND

Diabetes is a metabolic condition relating to the production or use of insulin by the body. Insulin is a hormone that allows the body to use glucose for energy, or store glucose as fat.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic patient carries a self-monitoring blood glucose (SMBG) monitor, which may require uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is unlikely that a diabetic will take a timely SMBG value, and further the diabetic will not know if his blood glucose value is going up (higher) or down (lower), due to limitations of conventional methods.

Consequently, a variety of non-invasive, transdermal (e.g., transcutaneous) and/or implantable sensors are being developed for continuously detecting and/or quantifying blood glucose values. Generally, in a diabetes management system, a transmitter associated with the sensor wirelessly transmits raw or minimally processed data for subsequent display and/or analysis at one or more display devices, which can include a mobile device, a server, or any other type of communication devices. A display device, such as a mobile device, may then utilize a trusted software application (e.g., approved and/or provided by the manufacturer of the sensor), which takes the raw or minimally processed data and provides the user with information about the user's blood glucose levels. Because diabetes management systems using such implantable sensors can provide more up-to-date information to users, they may reduce the risk of a user failing to regulate the user's blood glucose levels.

This background is provided to introduce a brief context for the summary and detailed description that follow. This background is not intended to be an aid in determining the scope of the claimed subject matter nor be viewed as limiting the claimed subject matter to implementations that solve any or all of the disadvantages or problems presented above.

SUMMARY

Certain embodiments provide a computer-implemented method for transmitting analyte data performed by a sensor electronics module of an analyte sensor system. The computer-implemented method includes obtaining the analyte data from an analyte sensor operatively coupled to the sensor electronics module, encrypting, in an application layer of a protocol stack of the sensor electronics module, the analyte data using a session key established between the analyte sensor system and a display device, and transmitting the encrypted analyte data to the display device Certain embodiments provide a computer-implemented method for receiving analyte data performed by a display device. The computer-implemented method includes receiving encrypted analyte data from an analyte sensor system and decrypting, in an application layer of a protocol stack of the display device, the analyte data using a session key established between the analyte sensor system and the display device.

Other aspects provide: an apparatus operable, configured, or otherwise adapted to perform any one or more of the aforementioned methods and/or those described elsewhere herein; a non-transitory, computer-readable media comprising instructions that, when executed by one or more processors of an apparatus, cause the apparatus to perform the aforementioned methods as well as those described elsewhere herein; a computer program product embodied on a computer-readable storage medium comprising code for performing the aforementioned methods as well as those described elsewhere herein; and/or an apparatus comprising means for performing the aforementioned methods as well as those described elsewhere herein. By way of example, an apparatus may comprise a processing system, a device with a processing system, or processing systems cooperating over one or more networks.

BRIEF DESCRIPTION OF THE DRAWINGS

FIG. 6 is a sequence diagram illustrating additional example operations for establishing and implementing ALE for communication between the analyte sensor system and the display device, according to certain embodiments disclosed herein.

FIG. 11 is a flow diagram illustrating example operations for transmitting analyte data performed by an analyte sensor system, according to certain embodiments disclosed herein.

DETAILED DESCRIPTION

Figure 1A:
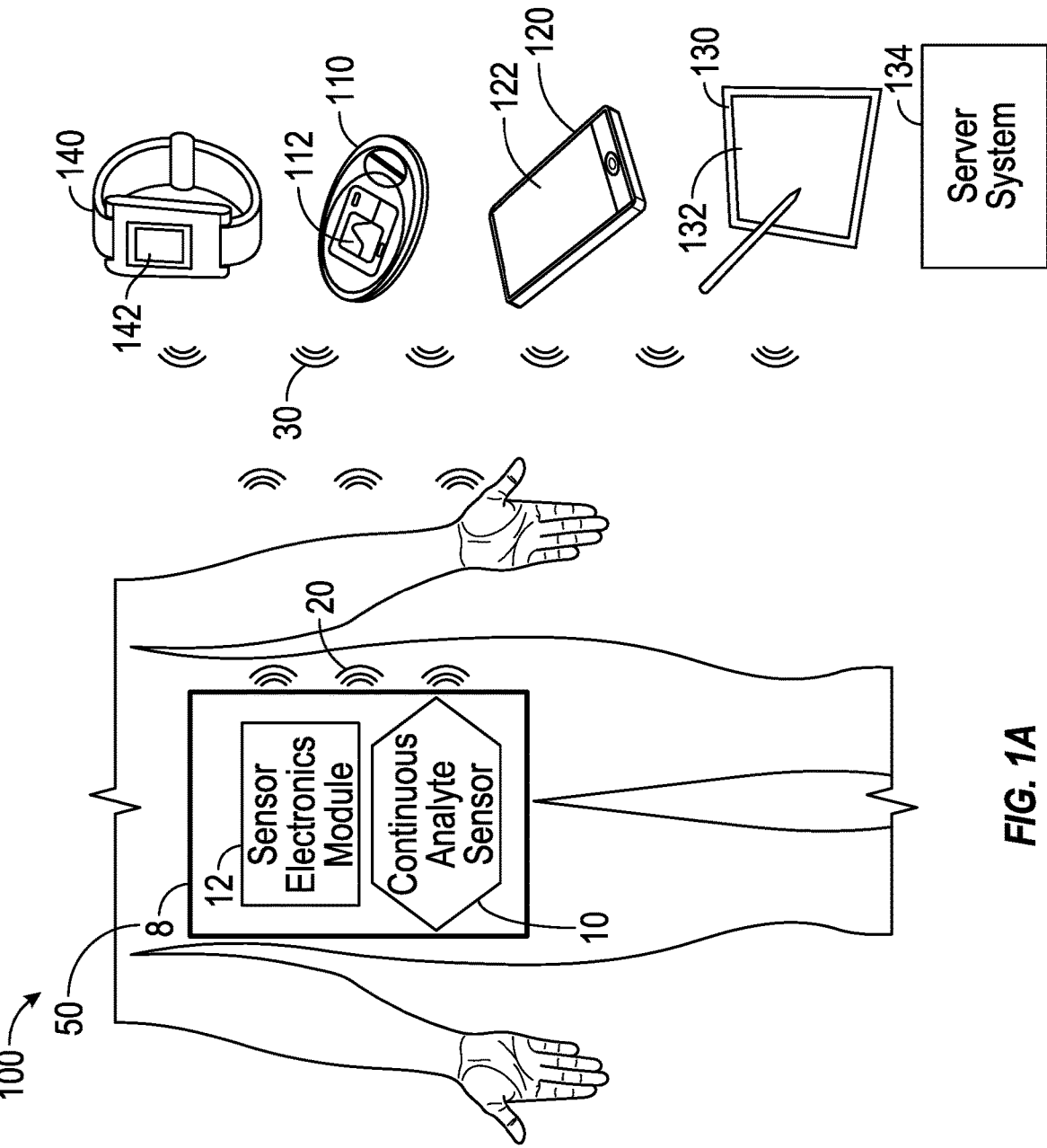
FIG. 1A illustrates an example health management system, according to certain embodiments disclosed herein.

A continuous glucose monitor (CGM) may include an analyte sensor system comprising an analyte senor (e.g., a glucose sensor) for measuring analyte (e.g., glucose) levels of a patient and a sensor electronics module for processing analyte sensor data or information from the analyte sensor. The analyte sensor may communicate raw sensor measurements to the sensor electronics module for processing. Thereafter, the analyte sensor system may then transmit corresponding analyte values (e.g., glucose values or levels) and/or the raw values to a patient's display device, such as a mobile phone. In order to connect with the display device for the initial time, the analyte sensor system is configured to transmit one or more invitation or broadcast or advertisement (also referred to as inviting or broadcasting or advertising, respectively) packets to the display device through one or more primary advertisement (hereinafter "invitation") channels.

In response to the invitation packets, the display device and the analyte sensor system may engage in a connection request/response exchange through the one or more primary invitation channels to establish a connection. Subsequently, the display device and the analyte sensor system may engage in authentication, pairing, and/or bonding through one or more data channels. In certain cases, the one or more primary invitation channels represent three out of forty different frequency channels, and the one or more data channels represent the remaining thirty-seven of the forty channels. The three frequency channels are designated for transmission of primary invitation packets, and the thirty-seven frequency channels are designated for transmission of data packets.

After bonding, the two devices exchange data (e.g., analyte values), and may then disconnect. Once the analyte sensor system and the display device have paired and bonded, at each of the devices, information about the other device and the bond that has been created with the other device is stored. For example, at the analyte sensor system, the display device is added to a "targeted device list," where information about the bond that has been created with the display device is stored and then used for reconnections. As a result, pairing and bonding will not be necessary during reconnections.

Reconnections may occur periodically, such as every five minutes or less so that the analyte sensor system can provide updated analyte values to the display devices. During a reconnection, the link between the analyte sensor system and the display device for exchanging data is secured using the information stored about the bond (e.g., authentication, encryption, and other similar information).

Typically, the analyte sensor system's communication stack (e.g., communication protocol stack, such as Bluetooth Low Energy (BLE) stack) includes an application layer and a lower protocol layer (e.g., BLE layer). Data, such as analyte values, may be managed at the application layer of the analyte sensor system's communication stack, while data connection/disconnections, security, pairing, bonding, and the like may be managed at the lower protocol layer (e.g., BLE layer). For example, while data, such as the analyte values, may be generated at the application layer of the analyte sensor system's communication stack, this data may be encrypted within the lower protocol layer/BLE layer of the analyte sensor system's communication stack.

However, while communication (e.g., communication of analyte values) using a BLE connection may be encrypted within the BLE layer between the analyte sensor system and the display device, this communication may be susceptible to certain vulnerabilities. For example, one such vulnerability is known as man-in-the-middle (MITM) attacks. MITM attacks commonly involve intercepting data between two parties in order to view/modify that data before relaying it on to the intended recipient. MITM attacks consist of controlling the back-and-forth communication between the two unsuspecting parties such that these two parties believe that they are communicating to each other but, in reality, the communication is being proxied by the MITM attacker. Any intercepted messages may be modified by the MITM attacker or left unaltered, depending on the intentions of the MITM attacker.

Other vulnerabilities associated with communication using a BLE connection relate to co-located applications on the display device. For example, in some cases, the display device may include an analyte sensor application used to communicate with the analyte sensor system. The display device may also include other unauthorized co-located applications (e.g., applications not authorized to communicate with the analyte sensor system). In such cases, these co-located applications may pose a vulnerability to the communication using the BLE connection as there may be a potential unauthorized re-use of system-wide pairing credentials established between the analyte sensor system and display device. In some cases, these co-located applications may use these pairing credentials to perform unauthorized communication with the analyte sensor system using an existing BLE connection. Additionally, in some cases, once information received from the analyte sensor system is decrypted by the display device, the information may be stored as unencrypted plaintext, which may be accessible by the unauthorized co-located applications. Additional co-located application vulnerabilities exist and are described herein.

Accordingly, to help eliminate or at least reduce the vulnerabilities discussed herein, aspects of the present disclosure provide techniques for implementing application layer encryption (ALE) or application layer security (ALS) within the BLE pairing process to provide secure end-to-end (e.g., application-to-application) encryption of data transmitted between the display device (e.g., mobile phone) and analyte sensor system. For example, unlike existing BLE security techniques in which data received from the analyte sensor system is BLE-decrypted by an operating system of the display device and is accessible as plaintext thereafter, when using ALE, the information received from the analyte sensor system may remain encrypted after BLE decryption by the operating system and may only be decrypted by an authorized application (e.g., analyte sensor application 121 of FIG. 1B) on the display device.

As a result, other unauthorized co-located applications on the display device may not be able to access information communicated between the analyte sensor system and display device since this information remains encrypted end-to-end and may only decrypted by an authorized application. Additionally, MITM attacks may be eliminated or greatly reduced when ALE is implemented. For example, assuming a MITM was able to exploit a vulnerability in BLE encryption, the information communicated between the display device and the analyte sensor system would still be encrypted using ALE, preventing the MITM from obtaining the information. More specifically, because the information is also encrypted using ALE and because ALE uses a different encryption scheme as compared to BLE encryption, the MITM would not be able to exploit the same BLE vulnerabilities to decrypt the ALE encryption. Further, because of the added layer of ALE, any future vulnerabilities discovered in the BLE communication protocol itself will not affect the security between the display device and the analyte sensor system.

The techniques described herein for performing application-layer security and communication are described more fully herein with respect to FIGS. 1A-1B and 2-13 below. It should be noted that although certain embodiments herein are described with respect to the management of diabetes, a glucose sensor system, and the transmission of glucose measurement between the devices, the protocols and techniques described herein are similarly applicable to any type of health management system that includes any type of analyte sensor (e.g., lactate sensor, ketone sensor, etc.).

Example Analyte Sensor System

FIG. 1A depicts a health management system 100 ("system 100"), such as a diabetes management system, that may be used in connection with certain embodiments of the present disclosure. Certain such embodiments may involve establishing application-layer security for communication within the health management system 100. Health management system 100 depicts aspects of analyte sensor system 8 (hereinafter "SS 8") that may be communicatively coupled to display devices 110, 120, 130, and 140, and/or to server system 134.

In certain embodiments, SS 8 is provided for measurement of an analyte in a host or a user. By way of an overview and an example, SS 8 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices, such as display devices 110, 120, 130, 140 and/or server system 134. U.S. App. No. 2019/0336053, which is incorporated herein in its entirety by reference, further describes an on-skin sensor assembly that, in certain embodiments, may be used in connection with SS 8.

In certain embodiments, SS 8 includes an analyte sensor electronics module 12 and an analyte sensor 10 associated with analyte sensor electronics module 12. In certain embodiments, analyte sensor electronics module 12 includes electronic circuitry associated with measuring and processing analyte sensor data or information, including algorithms associated with processing and/or calibration of the analyte sensor data/information. Analyte sensor electronics module 12 may be physically/mechanically connected to analyte sensor 10 and can be integral with (i.e., non-releasably attached to) or releasably attachable to analyte sensor 10.

Analyte sensor electronics module 12 may also be operatively coupled to analyte sensor 10, such that the components may be electromechanically coupled to one another (e.g., (a) prior to insertion into a patient's body, or (b) during the insertion into the patient's body). Analyte sensor electronics module 12 may include hardware, firmware, and/or software that enable measurement and/or estimation of levels of the analyte in a host/user via analyte sensor 10 (e.g., which may be/include a glucose sensor). For example, sensor electronics module 12 may include one or more potentiostats, a power source for providing power to analyte sensor 10, other components useful for signal processing and data storage, and a telemetry module for transmitting data from the sensor electronics module to one or more display devices. Electronics can be affixed to a printed circuit board (PCB) within SS 8, or platform or the like, and can take a variety of forms. For example, the electronics can take the form of an integrated circuit (IC), such as an Application-Specific Integrated Circuit (ASIC), a microcontroller, a processor, and/or a state machine.

Analyte sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

Analyte sensor 10 is configured to measure a concentration or level of the analyte in the host. The term analyte is further defined by U.S. App. No. 2019/0336053 In some embodiments, analyte sensor 10 comprises a continuous glucose sensor, such as a subcutaneous, transdermal (e.g., transcutaneous), or intravascular device. In some embodiments, analyte sensor 10 can analyze a plurality of intermittent blood samples. Analyte sensor 10 can use any method of glucose-measurement, including enzymatic, chemical, physical, electrochemical, spectrophotometric, polarimetric, calorimetric, iontophoretic, radiometric, immunochemical, and the like. Additional details relating to a continuous glucose sensor are provided in paragraphs [0072]-[0076] of U.S. application Ser. No. 13/827,577. Paragraphs [0072]-[0076] of U.S. application Ser. No. 13/827,577 are incorporated herein by reference. In certain embodiments, analyte sensor 10 may be configured to sense multiple analytes (e.g., glucose, potassium, lactate, and/or others).

With further reference to FIG. 1A, display devices 110, 120, 130, and/or 140 can be configured for displaying (and/or alarming) displayable sensor information that may be transmitted by sensor electronics module 12 (e.g., in a customized data package that is transmitted to the display devices based on their respective preferences). Each of display devices 110, 120, 130, or 140 may respectively include a display such as touchscreen display 112, 122, 132, and/or 142 for displaying sensor information and/or analyte data to a user and/or receiving inputs from the user. For example, a graphical user interface (GUI) may be presented to the user for such purposes. In certain embodiments, the display devices may include other types of user interfaces such as voice user interface instead of or in addition to a touchscreen display for communicating sensor information to the user of the display device and/or receiving user inputs. In certain embodiments, one, some, or all of display devices 110, 120, 130, 140 may be configured to display or otherwise communicate the sensor information as it is communicated from sensor electronics module 12 (e.g., in a data package that is transmitted to respective display devices), without any additional prospective processing required for calibration and/or real-time display of the sensor data.

The plurality of display devices 110, 120, 130, 140 depicted in FIG. 1A may include a custom or proprietary display device, for example, analyte display device, especially designed for displaying certain types of displayable sensor information associated with analyte data received from sensor electronics module 12 (e.g., a numerical value and/or an arrow, in certain embodiments). In certain embodiments, one of the plurality of display devices 110, 120, 130, 140 includes a smartphone, such as display device 150, based on an Android, iOS, or another operating system configured to display a graphical representation of the continuous sensor data (e.g., including current and/or historic data). In certain embodiments, health management system 100 further includes a medical delivery device (e.g., an insulin pump or pen). Sensor electronics module 12 may be configured to transmit sensor information and/or analyte data to medical delivery device. The medical delivery device (not shown) may be configured to administer a certain dosage of insulin or another medicament to the user based on the sensor information and/or analyte data (e.g., which may include a recommended insulin dosage) received from the sensor electronics module 12.

Figure 1B:
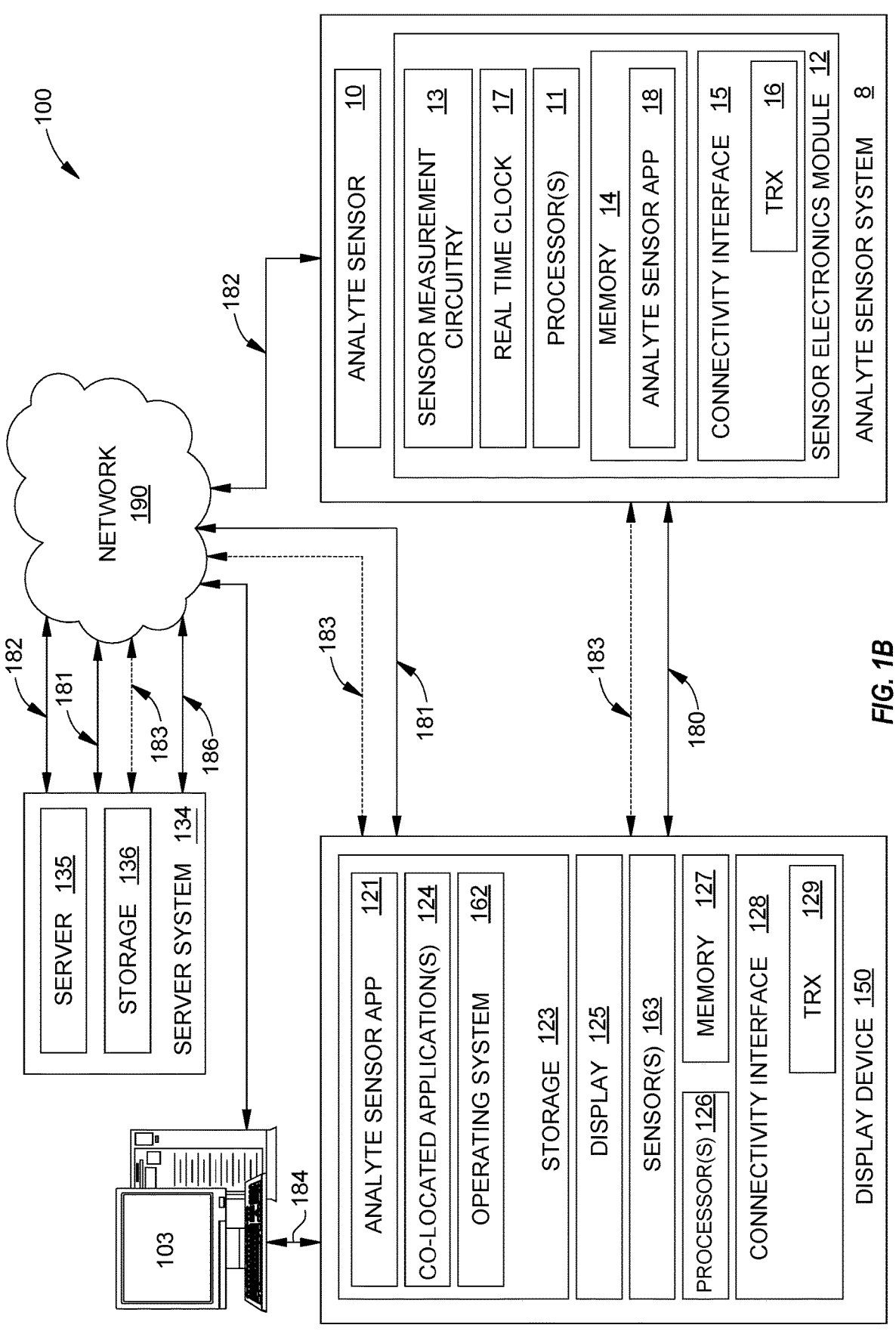
FIG. 1B illustrates the example health management system of FIG. 1A in more detail, according to certain embodiments disclosed herein.

FIG. 1B illustrates a more detailed view of health management system 100 including a display device 150 that is communicatively coupled to SS 8. In certain embodiments, display device 150 may be any one of display devices 110, 120, 130, and 140 of FIG. 1A. The communication path between SS 8 and display device 150 is shown as wireless communication path 180. In certain embodiments, SS 8 and display device 150 are configured to wirelessly communicate over wireless communication path 180 using low range and/or distance wireless communication protocols.

Examples of low range and/or distance wireless communication protocols include Bluetooth and Bluetooth Low Energy (BLE) protocols. In certain embodiments, other short range wireless communications may include Near Field Communications (NFC), radio frequency identification (RFID) communications, IR (infra-red) communications, optical communications. In certain embodiments, wireless communication protocols other than low range and/or distance wireless communication protocols may be used for wireless communication path 180, such as WiFi Direct. Display device 150 is also configured to connect to network 190 (e.g., local area network (LAN), wide area network (WAN), the Internet, etc.). For example, display device 150 may connect to network 190 via a wired (e.g., Ethernet) or wireless (e.g., WLAN, wireless WAN, cellular, Mesh network, personal area network (PAN) etc.) interface. Display device 150 is able to communicate with server system 134 through network 190. The communication path between display device 150 and server system 134 is shown as communication path 181 via network 190.

Note that, in certain embodiments, SS 8 may be able to independently (e.g., wirelessly) communicate with server system 134 through network 190. An independent communication path between SS 8 and server system 134 is shown as communication path 182. However, in certain other embodiments, SS 8 may not be configured with the necessary hardware/software to establish, for example, an independent wireless communication path with server system 134 through network 190. In such embodiments, SS 8 may communicate with server system 134 through display device 150. An indirect or pass-through communication path between SS 8 and server system 134 is shown as communication path 183.

In embodiments where display device 150 is a proprietary display device, such as display device 110 designed specifically for the communication of analyte data, display device 150 may not be configured with the necessary hardware/software for independently connecting to network 190. Instead, in certain such embodiments, display device 150 is configured to establish a wired or wireless communication path 184 (e.g., through a Universal System Bus (USB) connection) with computer device 103, which is configured to communicate with server system 134 through network 190. For example, computer device 103 may connect to network 190 via a wired (e.g., Ethernet) or wireless (e.g., WLAN, wireless WAN, cellular, etc.) interface. Note that in the embodiments described in relation to FIGS. 2-13, unless otherwise noted, display device 150 is assumed to be capable of independently communicating with server system 134 through network 190, independent of computer device 103.

Health management system 100 additionally includes server system 134, which in turn includes server 135 that is coupled to storage 136 (e.g., one or more computer storage systems, cloud-based storage systems and/or services, etc.). In certain embodiments, server system 134 may be located or execute in a public or private cloud. In certain embodiments, server system 134 is located or executes on-premises ("on-prem"). As discussed, server system 134 is configured to receive, collect, and/or monitor information, including analyte data and related information, as well as encryption/authentication information from SS 8 and/or display device 150. Such information may include input responsive to the analyte data or input (e.g., the user's glucose measurements and other physiological/behavioral information) received in connection with an analyte monitoring or sensor application running on SS 8 or display device 150. This information may be stored in storage 136 and may be processed, such as by an analytics engine capable of performing analytics on the information. An example of an analyte sensor application that may be executable on display device 150 is analyte sensor application 121, as further described below.

In certain embodiments, server system 134 at least partially directs communications between SS 8, and/or display device 150, for example, for facilitating authentication therebetween. Such communications include messaging (e.g., advertisement, command, or other messaging), message delivery, and analyte data. For example, in certain embodiments, server system 134 may process and exchange messages between SS 8 and display device 150 related to frequency bands, timing of transmissions, security, alarms, and so on. In certain embodiments, server system 134 may also update information stored on SS 8 and/or display device 150. In certain embodiments, server system 134 may send/receive information to/from SS 8 and or display device 150 in real-time or sporadically. Further, in certain embodiments, server system 134 may implement cloud computing capabilities for SS 8 and/or display device 150. In certain embodiments, server system 134 may send/receive information to/from SS 8 and/or display device 150 in real-time or sporadically.

FIG. 1B also illustrates the components of SS 8 in further detail. As shown, in certain embodiments, SS 8 includes analyte sensor 10 coupled to sensor electronics module 12. Sensor electronics module 12 includes sensor measurement circuitry (SMC) 13 that is coupled to analyte sensor 10 for processing and managing sensor data. SMC 13 may also be coupled to one or more processors 11. In some embodiments, the one or more processors 11 may perform part or all of the functions of the SMC 13 for obtaining and processing sensor measurement values from analyte sensor 10. The one or more processors 11 may also be coupled to one or more memories 14 and real time clock (RTC) 17 for storing and tracking sensor data. In some embodiments, the obtaining and processing of sensor measurement values may be managed by an analyte sensor application 18 stored in the one or more memories 14. For example, as shown, the one or more memories 14 stores analyte sensor application 18 that, when executed using the one or more processors 11, causes the one or more processors 11 to receive and process sensor measurement values from analyte sensor 10. Analyte sensor application 18 is also configured to execute the ALE protocols and algorithms described herein for providing ALE in collaboration with analyte sensor application 121 (or any other analyte related application, such as analyte partner application), executed on display device 150.

In addition, the one or more processors 11 may be further coupled to a connectivity interface 15, which includes a radio unit or transceiver (TRX) 16 for sending sensor data and receiving requests and commands from an external device, such as display device 150. As used herein, the term transceiver generally refers to a device or a collection of devices that enable SS 8 to (e.g., wirelessly) transmit and receive data. SS 8 may further include the one or more memories 14 and RTC 17 for storing and tracking sensor data. It is contemplated that, in some embodiments, the SMC 13 may carry out all the functions of the one or more processors 11 and vice versa.

Transceiver 16 may be configured with the necessary hardware and wireless communications protocols for enabling wireless communications between SS 8 and other devices, such as display device 150 and/or server system 134. For example, as described above, transceiver 16 may be configured with the necessary hardware and communication protocols to establish a Bluetooth or BLE connection with display device 150. As one of ordinary skill in the art appreciates, in such an example, the necessary hardware may include a Bluetooth or BLE security manager and/or other Bluetooth or BLE related hardware/software modules configured for Bluetooth or BLE communications standards. In some embodiments where SS 8 is configured to establish an independent communication path with server system 134, transceiver 16 may be configured with the necessary hardware and communication protocols (e.g., long range wireless cellular communication protocol, such as, GSM, CDMA, LTE, VoLTE, 3G, 4G, and 5G communication protocols, WiFi communication protocols, such as 802.11 communication protocols, etc.) for establishing a wireless connection to network 190 to connect with server system 134. As discussed elsewhere, other short range protocols, may also be used for communication between display device 150 and a SS 8 such as NFC, RFID, etc.

FIG. 1B similarly illustrates the components of display device 150 in further detail. As shown, display device 150 includes connectivity interface 128, one or more processors 126, the one or more memories 127, one or more sensor(s) 163, a display 125 for presenting a graphical user interface (GUI), and a storage 123. A bus (not shown here) may be used to interconnect the various elements of display device 150 and transfer data between these elements. Connectivity interface 128 includes a transceiver (TRX) 129 used for receiving sensor data from SS 8 and for sending requests, instructions, and/or data to SS 8 as well as server system 134. Transceiver 129 is coupled to other elements of display device 150 via connectivity interface 128 and/or the bus. Transceiver 129 may include multiple transceiver modules operable on different wireless standards. For example, transceiver 129 may be configured with one or more communication protocols, such as wireless communication protocol(s) for establishing a wireless communication path with network 190 and/or low range wireless communication protocol(s) (e.g., Bluetooth or BLE) for establishing a wireless communication path 180 with SS 8. Additionally, connectivity interface 128 may in some cases include additional components for controlling radio and/or wired connections, such as baseband and/or Ethernet modems, audio/video codecs, and so on. Sensor(s) 163 may include, but is not limited to, accelerometer(s), gyroscope(s), global positioning system (GPS) sensor(s), heart rate sensor(s), etc. Note that while sensor(s) 163 are shown integral to the display device, in certain embodiments, one or more of sensor(s) 163 be standalone sensors (e.g., separate from the display device 150).

In some embodiments, when a standardized communication protocol is used between display device 150 and SS 8, commercially available transceiver circuits may be utilized that incorporate processing circuitry to handle low level data communication functions such as the management of data encoding, transmission frequencies, handshake protocols, security, and the like. In such embodiments, the one or more processors 126 of display device 150 and/or the one or more processors 11 of SS 8 may not need to manage these activities, but instead provide desired data values for transmission, and manage high level functions such as power up or down, set a rate at which messages are transmitted, and the like. Instructions and data values for performing these high level functions can be provided to the transceiver circuits via a data bus and transfer protocol established by the manufacturer of transceivers 129 and 16. However, in embodiments where a standardized communication protocol is not used between transceivers 129 and 16 (e.g., when non-standardized or modified protocols are used), processors 126 and 11 may be configured to execute instructions associated with proprietary communications protocols (e.g., one or more of the communications protocols described herein) to control and manage their respective transceivers. In addition, when non-standardized or modified protocols are used, customized circuitries may be used to service such protocols.

The one or more processors 126 may include processor sub-modules, including, by way of example, an applications processor that interfaces with and/or controls other elements of display device 150 (e.g., connectivity interface 128, analyte sensor application 121 (hereinafter "sensor application 121"), co-located application(s) 124, display 125, sensor(s) 163, one or more memories 127, storage 123, etc.). In certain embodiments, the one or more processors 126 is configured to perform functions related to device management, such as, for example, managing lists of available or previously paired devices, information related to network conditions (e.g., link quality and the like), information related to the timing, type, and/or structure of messaging exchanged between SS 8 and display device 150, and so on. The one or more processors 126 may further be configured to receive and process user input, such as, for example, a user's biometric information, such as the user's finger print (e.g., to authorize the user's access to data or to be used for authorization/encryption of data, including analyte data), as well as analyte data.

The one or more processors 126 may include and/or be coupled to circuitry such as logic circuits, memory, a battery and power circuitry, and other circuitry drivers for periphery components and audio components. The one or more processors 126 and any sub-processors thereof may include logic circuits for receiving, processing, and/or storing data received and/or input to display device 150, and data to be transmitted or delivered by display device 150. As described above, the one or more processors 126 may be coupled by a bus to display 125, connectivity interface 128, storage 123, etc. Hence, the one or more processors 126 may receive and process electrical signals generated by these respective elements and thus perform various functions. By way of example, the one or more processors 126 may access stored content from storage 123 and the one or more memories 127 at the direction of analyte sensor application 121, and process the stored content to be displayed by display 125. Additionally, the one or more processors 126 may process the stored content for transmission via connectivity interface 128 to SS 8 and/or server system 134. Display device 150 may include other peripheral components not shown in detail in FIG. 1B.

In certain embodiments, the one or more memories 127 may include volatile memory, such as random access memory (RAM) for storing data and/or instructions for software programs and applications, such as analyte sensor application 121 and co-located application(s) 124. Display 125 presents a GUI associated with operating system 162 and/or analyte sensor application 121. In various embodiments, a user may interact with analyte sensor application 121 via a corresponding GUI presented on display 125. By way of example, display 125 may be a touchscreen display that accepts touch input. Analyte sensor application 121 may process and/or present analyte-related data received by display device 150 and present such data via display 125. Additionally, analyte sensor application 121 may be used to obtain, access, display, control, and/or interface with analyte data and related messaging and processes associated with SS 8 (e.g., and/or any other medical device (e.g., insulin pump or pen) that are communicatively coupled with display device 150), as is described in further detail herein. Further, as illustrated, the display device 150 includes co-located applications, which may not be authorized to obtain, access, display, control, and/or interface with analyte data and related messaging and processes associated with SS 8.

Storage 123 may be a non-volatile storage for storing software programs, instructions, data, etc. For example, storage 123 may store analyte sensor application 121 that, when executed using the one or more processors 126, for example, receives input (e.g., by a conventional hard/soft key or a touch screen, voice detection, or other input mechanism), and allows a user to interact with the analyte data and related content via display 125. Similarly, storage 123 may store co-located application(s) 124 that, when executed using the one or more processors 126, for example, receives input (e.g., by a conventional hard/soft key or a touch screen, voice detection, or other input mechanism), and allows a user to interact with the other non-analyte related data and related content via display 125. In some cases, examples of the co-located application(s) 124 may include a clock application, a text messaging application, a social media application, or any other type of application stored on the display device 150 that is not authorized to obtain, access, display, control, and/or interface with analyte data and related messaging and processes associated with SS 8.

In various embodiments, storage 123 may also store user input data and/or other data collected by display device 150 (e.g., input from other users gathered via analyte sensor application 121). Storage 123 may further be used to store volumes of analyte data received from SS 8 (or any other medical data received from other medical devices (e.g., insulin pump, pen, etc.) for later retrieval and use, e.g., for determining trends and triggering alerts.

As described above, SS 8, in certain embodiments, gathers analyte data from analyte sensor 10 and transmits the same or a modified version of the collected data to display device 150. Data points regarding analyte values may be gathered and transmitted over the life of analyte sensor 10 (e.g., in the range of 1 to 30 days or more). New measurements may be transmitted often enough to adequately monitor glucose levels. In certain embodiments, rather than having the transmission and receiving circuitry of each of SS 8 and display device 150 continuously communicate, SS 8 and display device 150 may regularly and/or periodically establish a communication channel among each other. Thus, in such embodiments, SS 8 may, for example, communicate with display device 150 at predetermined time intervals. The duration of the predetermined time interval can be selected to be long enough so that SS 8 does not consume too much power by transmitting data more frequently than needed, yet frequent enough to provide substantially real-time sensor information (e.g., measured glucose values or analyte data) to display device 150 for output (e.g., via display 125) to the user. While the predetermined time interval is every five minutes in some embodiments, it is appreciated that this time interval can be varied to be any desired length of time. In other embodiments, transceivers 129 and 16 may be continuously communicating. For example, in certain embodiments, transceivers 129 and 16 may establish a session or connection there between and continue to communicate together until the connection is lost.

Analyte sensor application 121 may be downloaded, installed, and initially configured/setup on display device 150. For example, display device 150 may obtain analyte sensor application 121 from server system 134, or from another source, such as an application store or the like, via a network, e.g., network 190. Following installation and setup, analyte sensor application 121 may be configured to access, process, and/or interface with analyte data (e.g., whether stored on server system 134, locally from storage 123, from SS 8, or any other medical device). By way of example, analyte sensor application 121 may present a menu that includes various controls or commands that may be executed in connection with the operation of SS 8, display device 150, one or more other display devices (e.g., display device 110, 130, 140, etc.), and/or one or more other partner devices, such as an insulin pump. For example, analyte sensor application 121 may be used to interface with or control other display and/or partner devices, for example, to deliver or make available thereto analyte data, including for example by receiving/sending analyte data directly to the other display and/or partner device and/or by sending an instruction for SS 8 and the other display and/or partner device to be connected.

After downloading analyte sensor application 121, as one of the initial steps, the user may be directed by analyte sensor application 121 to wirelessly connect display device 150 to the user's SS 8, which the user may have already placed on their body. A wireless communication path 180 between display device 150 and SS 8 allows SS 8 to transmit analyte measurements to display device 150 and for the two devices to engage in any of the other interactions described above.

Example Communication Protocol Architecture

Figure 2:
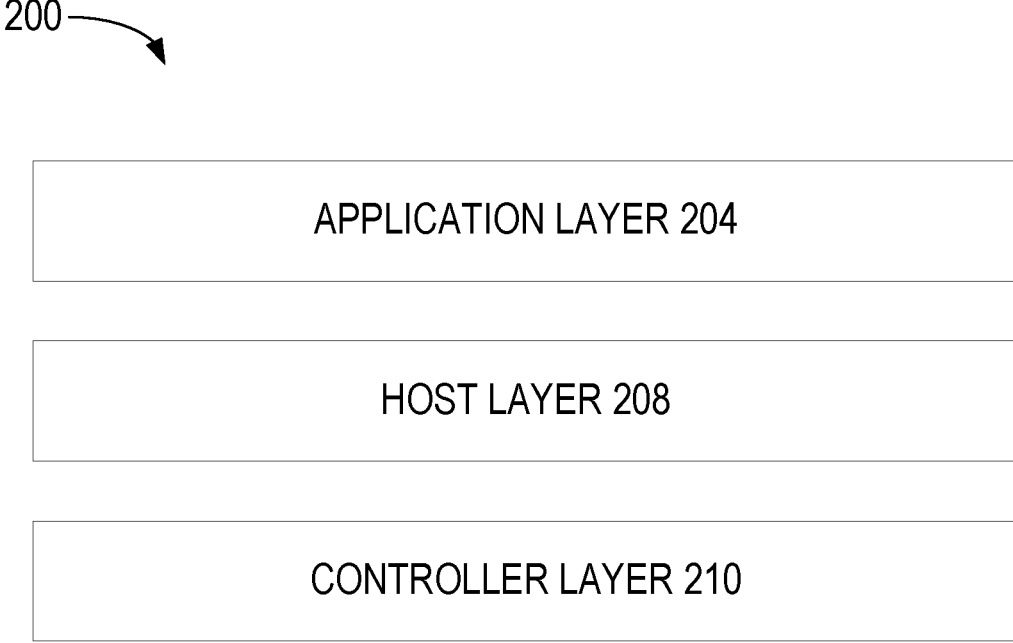
FIG. 2 illustrates an example communication protocol architecture, according to certain embodiments disclosed herein.

FIG. 2 illustrates an example communication protocol architecture 200 (e.g., a protocol stack), according to certain embodiments. In some embodiments, the communication protocol architecture 200 may be implemented in the SS 8 and/or the display device 150. In the depicted embodiment, the communication protocol architecture 200 (also referred to as a communication protocol stack) includes an application layer 204, a host layer 208, and a controller layer 210. The application layer 204 is the highest layer(s) of the communication protocol architecture 200 and generally provides application layer services, device roles and modes, and/or connection management for one or more applications being executed in the SS 8 and/or display device 150, such as the analyte sensor application 18 of the SS 8, the analyte sensor application 121 of the display device 150, and/or the co-located application(s) 124 of the display device 150. The host layer 208 and controller layer 210 are the lower layer(s) of the communication protocol architecture 200. As used herein, a "lower protocol layer" may refer to the host layer 208 and/or controller layer 210.

The controller layer 210 may provide physical layer (PHY) services, including, for example, analog communication circuitry responsible for translation of digital data over the air. The host layer 208 is generally responsible for tasks, such as (i) inviting, scanning, and creating/maintaining connections, (ii) encapsulating the data received from upper layers and generating packets for transmission over via the controller layer 210, (iii) performing packet error-detecting, (iv) encryption/decryption of the communication, (v) segmentation and reassembly operations for packets exchanged between the application layer 204 and the controller layer 210, and the like.

Although not shown in FIG. 2, in certain embodiments, the communication protocol architecture 200 may also include a host controller interface (HCI), which is a thin layer that transports commands and events between the host layer 208 and controller layer 210.

As described in greater detail below, certain aspects described herein provide techniques for implementing data security at the higher layer(s) of the communication stack (e.g., application layer 204) as opposed to at the lower layer(s) of the communication stack (e.g., host layer 208 and/or controller layer 210), in order to address a number of security vulnerabilities, including, for example, vulnerabilities associated with MITM attacks and vulnerabilities associated with unauthorized co-located applications on a display device.

Aspects Related to Wireless Communication Security for Analyte Monitoring Systems As discussed, in conventional communication protocols used for exchanging analyte data, data security (e.g., integrity, authentication, and encryption) is typically implemented at a lower protocol layer (e.g., host layer 208 and/or controller layer 210) of the communication stack (e.g., communication protocol architecture 200). In some embodiments, this lower protocol layer may be an example of a Bluetooth Low Energy (BLE) layer within a BLE communication stack. As noted, however, implementing such data security at the lower protocol layer of the communication stack may leave communication of data between the SS 8 and the display device 150 susceptible to a number of vulnerabilities. In some embodiments, the SS 8 may generally be referred to as a transmitter.

As discussed above, one such vulnerability relates to MITM attacks, which commonly involve intercepting data between two parties in order to view and/or modify the data before relaying it on to the intended recipient. MITM attacks consist of controlling the back-and-forth communication between the two unsuspecting parties such that these two parties believe that they are communicating to each other but, in reality, the communication is being proxied by the MITM attacker. Any intercepted messages may be modified by the MITM attacker or left unaltered, depending on the intentions of the MITM attacker.

Another type of vulnerability that BLE technology may be susceptible to relates to unauthorized co-located applications (e.g., co-located application(s) 124 illustrated in FIG. 1B) on the display device 150. One such vulnerability related to co-located applications includes the potential re-use of system-wide BLE pairing credentials, established between the SS 8 and the display device 150, by other unauthorized co-located applications on the display device 150 (e.g., applications not authorized to communicate with the SS 8). For example, on the display device 150, an operating system of the display device 150 (e.g., operating system 162 of FIG. 2) may control a BLE bond and the encryption/decryption of messages received transmitted to and received from the SS 8. Once information that has been received from the SS 8 is decrypted by the operating system of the display device 150, this information may be accessed as unencrypted plaintext. This may present a security issue since other unauthorized co-located applications installed on the display device 150 may be able to access (e.g., read, write, etc.) the plaintext information (e.g., BLE pairing credentials) received from the SS 8.

Further, BLE pairing credentials (e.g., security keys) that are stored on the display device 150 may be implicitly available to all applications on the display device 150, rather than being restricted only to the application that originally triggered the BLE pairing process between the SS 8 and display device 150. Not only is an unauthorized application able to access potentially sensitive information from the SS 8, a user of the display device 150 may be unaware of the fact that data access by an unauthorized application is taking place since there is no indication during link re-encryption and subsequent attribute access.

Another vulnerability related to co-located applications includes the potential re-use of BLE connections. For example, on the display device 150 (e.g., a mobile smartphone), a BLE peripheral in the display device 150 may be used concurrently by multiple applications. As a result, an unauthorized co-located application may, instead of scanning for BLE devices over the air, search on the display device 150 for connected BLE devices, such as the SS 8. If a continuous glucose monitoring application on the display device 150 happens to be in communication with the SS 8 at the same time, a list with a reference to the connected SS 8 may be returned to the unauthorized co-located application on the display device 150. The unauthorized co-located application may then be able to directly connect to the SS 8 and read/write to the characteristics on it (including those that are pairing protected), without the need to create a new connection to the SS 8. This, again, may be performed surreptitiously, without the user of the display device 150 being aware of the data access.

Additionally, an unauthorized co-located application reusing a BLE connection may only require minimum permissions, making it appear less invasive in the eyes of a user, since the unauthorized co-located application may not request any permission that involves user privacy. This would be advantageous for a malicious application to gain access to the transmitted unbeknownst to the user. Regardless of whether there is a malicious application or not, this reuse of the BLE connection serves as a vehicle for unauthorized third-party applications on the display device 150 to be used within an ecosystem of a continuous glucose monitor, such as the SS 8.

Accordingly, to help eliminate or at least reduce the vulnerabilities discussed above, aspects of the present disclosure provide techniques for implementing application layer encryption (ALE) within a BLE connection process (e.g., pairing process) between the SS 8 and display device 150 to provide secure end-to-end encryption of data transmitted between the display device 150 and the SS 8. For example, unlike existing BLE security techniques in which encryption of data communicated between the display device 150 and SS 8 occurs solely within a lower protocol layer (e.g., BLE layer) of a communication stack of the display device 150 and SS 8, when using ALE, the data may first be encrypted within an application layer (e.g., application layer 204) of the communication stack (e.g., communication protocol architecture 200) of the SS 8 and/or display device 150 and then encrypted again within the lower protocol layer (e.g., host layer 208 and/or controller layer 210) of the communication stack of the SS 8 and/or display device 150.

As a result, unlike existing BLE security techniques in which data received from the SS 8 is BLE-decrypted by the operating system of the display device 150 and is accessible as plaintext thereafter, when using ALE, even though the data received from the SS 8 is BLE-decrypted by the operating system of the display device 150, the data remains encrypted (e.g., via ALE encryption) after BLE decryption and may only be decrypted by an authorized application on the display device 150. Accordingly, other unauthorized co-located applications on the display device 150 are not able to access information communicated between the SS 8 and display device 150 since this information remains encrypted end-to-end (e.g., application layer-to-application layer) and may only be decrypted by an authorized application in the display device 150 and/or SS 8. In some embodiments, an authorized application is an application that is authorized or licensed (e.g., by a manufacturer or retailer of the SS 8) to communicate with the SS 8. The authorized application may also be an application that is authorized or licensed (e.g., by a manufacturer or retailer of the SS 8) to establish and/or access application layer security key(s) (e.g., an ALE session key) and to use the application layer security key(s) to encrypt and/or decrypt data communicated between the SS 8 and the display device 150.

Additionally, MITM attacks may be eliminated since, even if a MITM attacker were to exploit a vulnerability in BLE encryption, the data communicated between the display device 150 and SS 8 would still be encrypted using ALE. In other words, even if a MITM attacker were to break the encryption performed at the lower protocol layer (e.g., BLE layer), the MITM attacker would still not be able to recover/understand the data since it would still be encrypted using ALE. Further, because of the added layer of ALE, any future vulnerabilities discovered in the BLE communication protocol itself would not affect the security between the display device 150 and the SS 8.

It should be appreciated that the techniques presented below for implementing ALE security or encryption may be used in different scenarios. For example, a first scenario may involve the use of the SS 8 and the display device 150 by a patient or user in a home setting. In this scenario, for example, the SS 8 and display device 150 may be used by only one user. For example, in the home setting scenario, the display device 150 of the user may perform an ALE setup procedure, as described below, to establish a connection with the SS 8 of the user and to establish a session key for ALE encryption. Thereafter, the display device 150 and the SS 8 of the user may communicate with each other using ALE encryption.

Another scenario may involve a hospital setting in which multiple users or SS 8s may be used with a single display device 150. For example, in some cases, while in a hospital, a first patient may be assigned a particular hospital-owned display device 150. The hospital-owned display device 150 may perform an ALE setup procedure, as described below, to establish a connection with an SS 8 of the first patient and to establish a session key for ALE encryption. Thereafter, the hospital-owned display device 150 and the SS 8 of the first patent may communicate with each other using ALE encryption. In some cases, when the first patient has finished their stay at the hospital, the hospital-owned display device 150 may be reassigned to a second patient. The hospital-owned display device 150 may then perform the ALE setup procedure again to establish a connection with an SS 8 of the second patient and to establish another session key for ALE encryption. Thereafter, the hospital-owned display device 150 and the SS 8 of the second patent may communicate with each other using ALE encryption.

First Example ALE Setup Procedure

Figure 3:
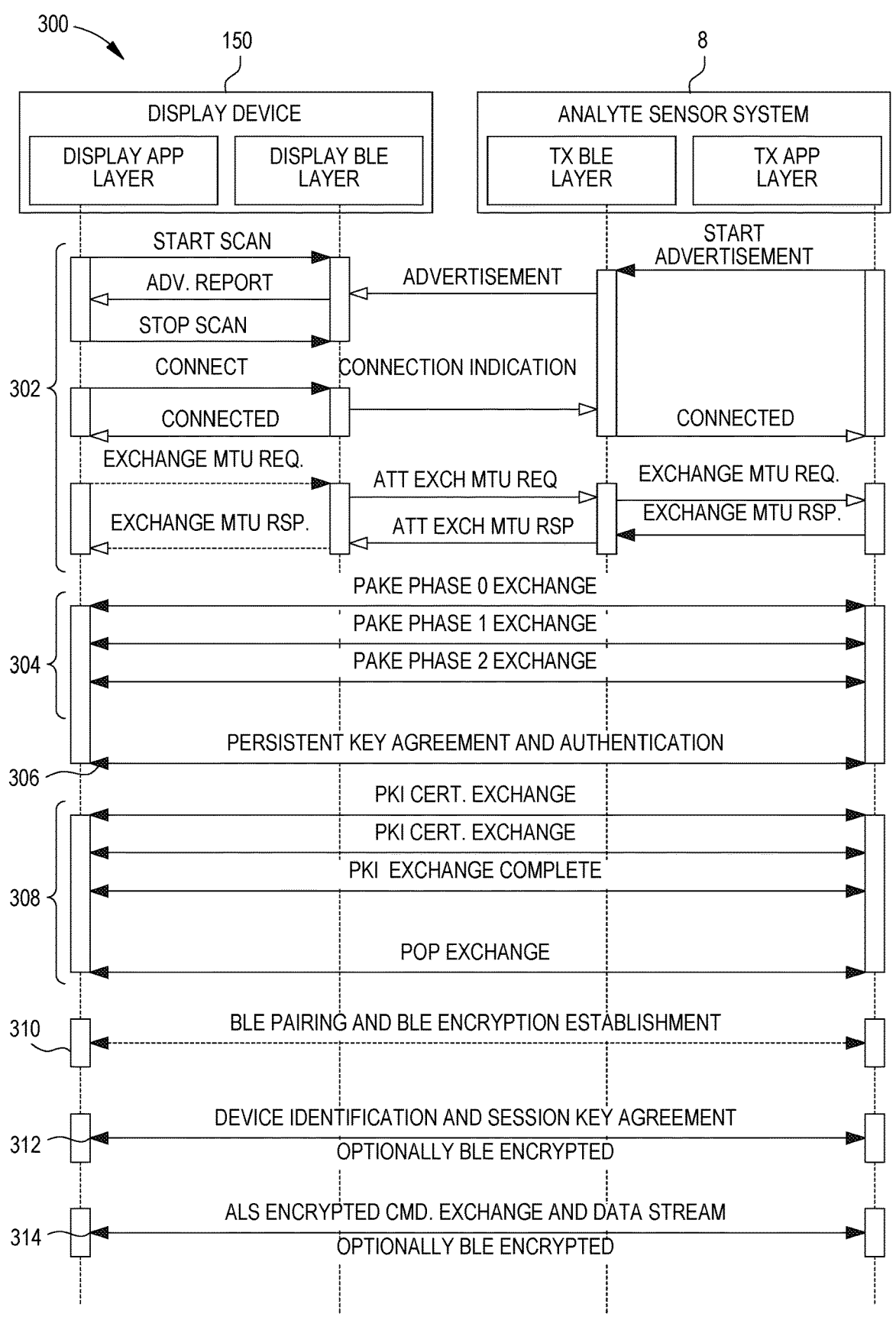
FIG. 3 is a sequence diagram illustrating example operations for establishing and implementing application layer encryption (ALE) for communication between an analyte sensor system and a display device, according to certain embodiments disclosed herein.

FIG. 3 is a sequence diagram illustrating example operations of an example ALE setup procedure 300 that may be performed by an SS 8 and a display device 150 to generate a session key for ALE encryption, according to certain embodiments described herein. For example, the operations illustrated in the ALE setup procedure 300 may be performed by the SS 8 and display device 150 for establishing and implementing ALE for communication between the SS 8 and display device 150. As will be described in greater detail below, the operations of the example ALE setup procedure 300 may involve using a shared secret, generated based on a juggling password authenticated key exchange (PAKE) protocol using elliptic curve cryptography (EC-JPAKE), to generate a set of persistent keys. The set of persistent keys may then be used to generate a session key for ALE encryption.

It should be appreciated that one or more of the operations of the ALE setup procedure 300 may be performed by one or more components of the SS 8, such as the sensor electronics module 12, including the one or more processors 11 and/or one or more memories 14. Similarly, one or more of the operations of the ALE setup procedure 300 may also be performed by one or more components of the display device 150, such as the one or more processors 126, the one or more memories 127, and/or the transceiver 129 of the connectivity interface 128.

As shown, the example operations begin in step 302 with the SS 8 and the display device 150 performing a scanning and advertising procedure to allow the SS 8 and the display device 150 to discover each other and establish a connection, such as a Bluetooth or Bluetooth Low Energy (BLE) connection.

As shown in step 302, the SS 8 and display device 150 may optionally perform a maximum data transfer unit (MTU) requirement exchange procedure to determine an MTU size for ALE. For example, in some cases, a default MTU size at an application layer (e.g., of the communication protocol architecture 200 of the SS 8 and/or display device 150) may be 20 bytes. However, in some cases, the default MTU size may not be sufficient to allow for ALE due to an overhead associated with commands exchanged between the display device 150 and the SS 8. Accordingly, in some embodiments, the display device 150 may transmit a request to the SS 8 to increase the MTU size (e.g., to 24 or more bytes). The SS 8 may, thereafter, transmit a response to the display device 150, indicating whether the request to increase the MTU size was accepted. In some cases, the response may indicate a maximum MTU size that the SS 8 supports. Thereafter, the MTU size agreed upon during the MTU requirement exchange procedure may then be used for communication of data between the SS 8 and display device 150.

Thereafter, as shown in step 304, the SS 8 and display device 150 engage in a patient centric authentication procedure to authenticate a user of the SS 8 and display device 150 (e.g., to authenticate that the user is authorized to use the display device 150 and/or SS 8). The patient centric authentication procedure may involve executing a cryptographic key exchange algorithm, examples of which include, but are not limited to, EC-JPAKE, a Diffie-Hellman (DH) key exchange algorithm, an Elliptic Curve Diffie-Hellman (ECDH), etc.

In particular, in certain embodiments, the cryptographic key exchange algorithm performed in step 304 may be based on a key-agreement protocol. A key agreement protocol is a protocol whereby two or more parties can agree on a shared secret in such a way that both influence the outcome. Here, using the cryptographic key exchange algorithm, the SS 8 and display device 150 may establish a shared secret (also known as a secret key or encryption key or cryptographic key). For example, the SS 8 and the display device 150 may each establish the shared secret by executing the cryptographic key exchange algorithm at the application layer. In some cases, the shared secret may comprise a 32-byte shared secret.

Thereafter, once the shared secret has been generated, the SS 8 and display device 150 may perform a persistent key agreement and authentication procedure, as shown in step 306 in FIG. 3. The SS 8 and display device 150 may perform the persistent key agreement and authentication procedure to authenticate the shared key produced/generated at each of the SS 8 and display device 150. In other words, SS 8 and display device 150 may perform the persistent key agreement and authentication procedure to ensure that the same shared secret was generated at both the SS 8 and display device 150. Additional details regarding the persistent key agreement and authentication procedure performed in step 306 of FIG. 3 will be described with respect to FIG. 4.

Thereafter, as shown in step 308, the SS 8 and display device 150 perform a device-centric authentication procedure, such as a public key infrastructure (PKI) certification exchange procedure, to authenticate that each of the SS 8 and display device 150 is an authorized device. PKI refers to a set of roles, policies, hardware, software, and procedures for creating managing, distributing, using, storing, and revoking certificates as well as managing public-key encryption. In a typical PKI scheme, each device may generate or be configured with a key-pair, including a public key and a private key. When information is encrypted using the private key, only the corresponding public key can be used to decrypt that information and vice versa. A public key of the device may be disseminated widely while the device's private key is typically known only to the device and not shared with any other devices. In some embodiments, before performing the operations illustrated in FIG. 3, display device 150 first obtains authentication data, including a public and private key-pair, from a server system (e.g., server system 134) during a set-up process of a sensor application (e.g., analyte sensor application 121), which executes on display device 150.

PKI binds public keys with respective identities of devices. The binding is established through a process of registration and issuance of certificates at and by a certificate authority (CA). The primary role of the CA is to digitally sign and publish the public key bound to a given device. The CA's own private key is used so that trust in the user key relies on one's trust in the validity of the CA's key. In certain embodiments, the server system 134 performs the functions of a root CA (RCA) by issuing and, directly or indirectly, signing certificates of display device 150 and SS 8. An RCA is an entity that verifies all other entities in a system.

Accordingly, as shown in step 308, display device 150 and SS 8 perform the PKI certification exchange procedure or "PKI protocol". FIGS. 4C and 11 and paragraphs [0212]-[0223] of U.S. application Ser. No. 17/308,754, filed May 5, 2021, and entitled "SECURE HEALTH MANAGEMENT SYSTEM", which is incorporated herein by reference in its entirety (hereinafter referred to as the "'754 application"), provide an example of display device 150 and SS 8 performing the PKI protocol. Display device 150 uses its public and private key-pair when performing PKI with SS 8. In some embodiments, SS 8 is configured with its key-pair during the manufacturing process of SS 8. One example of display device 150 obtaining authentication data from a server system is described in FIGS. 2A and 2B and paragraphs [0063]-[0065] of U.S. application Ser. No. 17/308, 754, filed May 5, 2021, and entitled "SECURE HEALTH MANAGEMENT SYSTEM", which is incorporated herein by reference in its entirety (hereinafter referred to as the "'754 application").

Thereafter, as shown in step 310, the SS 8 and display device 150 may optionally engage in a BLE paring and BLE encryption establishment procedure. In some embodiments, the BLE paring and BLE encryption establishment may be performed to generate one or more BLE security keys that may be used by the SS 8 and display device 150 for encrypting data at a lower protocol layer or BLE layer (e.g., host layer 208 and/or controller layer 210). In some embodiments, encryption of the data (e.g., blood glucose values or other analyte values of a user determined or measured by the SS 8) at the lower protocol layer using the BLE security key may be performed in addition to ALE encryption performed on the data at the application layer using an application-layer-based ALE session key established between the SS 8 and display device 150, as described below with respect to step 312 in FIG. 3.

For example, as shown in step 312, the SS 8 and display device 150 may perform a device identification and session key agreement procedure. The device identification and session key agreement procedure allows the SS 8 to resolve an identity of the display device 150 by searching for a matching identity among (previously) known display devices 120. Additionally, the device identification and session key agreement procedure may be used to generate a session key used for forward secrecy and to allow for recovering from an encryption/decryption failure due to loss of synchronization in packet counter values. In other words, the session key may be used to quickly re-authenticate and encrypt communication between the display device 150 and SS 8 in the event of an encryption/decryption failure. In some embodiments, as will be described, the session key may be used for application layer encryption to encrypt data (e.g., blood glucose values and/or other analyte values) at the application layer of the SS 8 and/or display device 150. As noted above, the encryption of data at the application layer may be performed in addition to encryption of the data at the lower protocol layer (e.g., BLE layer) using the BLE security key. Additional details regarding the device identification and session key agreement procedure performed in step 312 of FIG. 3 will be described with respect to FIG. 5.

Thereafter, as shown in step 314 of FIG. 3, the SS 8 and display device 150 may engage in routine communication of ALE-encrypted commands and data. For example, in some embodiments, data for transmission by the SS 8 (e.g., blood glucose values) may first be encrypted at an application layer of the SS 8 based on the session key generated in the device identification and session key agreement procedure, for example, to generate ALE-encrypted data. Thereafter, the ALE-encrypted data may then be provided to a lower protocol layer of the SS 8 (e.g., the host layer 208 and/or controller layer 210). In some embodiments, the ALE-encrypted data may be encrypted again by the lower protocol layer of the SS 8 using one or more security keys, such as the BLE security key discussed above, to generate two-level encrypted data (e.g., twice-encrypted data).

Thereafter, the two-level encrypted data may then be transmitted to the display device 150. The display device 150 may then perform complementary decryption operations to decrypt the two-level encrypted data. For example, a lower protocol layer (e.g., BLE layer) may first decrypt the data using the BLE security key to obtain the ALE-encrypted data. Thereafter, the lower protocol layer may provide the ALE-encrypted data to an application layer of the display device 150. An authorized application in the application layer of the display device 150 may then use the session key generated during the device identification and session key agreement procedure performed in step 312 of FIG. 3 to decrypt the ALE-encrypted data for a second time to recover the data generated by the application layer of the SS 8 (e.g., the blood glucose values and/or other analyte values).

Persistent Key Agreement and Authentication Procedure

As noted above, FIG. 4 illustrates example operations 400 that may be performed by the SS 8 (e.g., the sensor electronics module 12 of the SS 8) and the display device 150 when performing the persistent key agreement and authentication procedure described in step 306 in FIG. 3.

Figure 4:
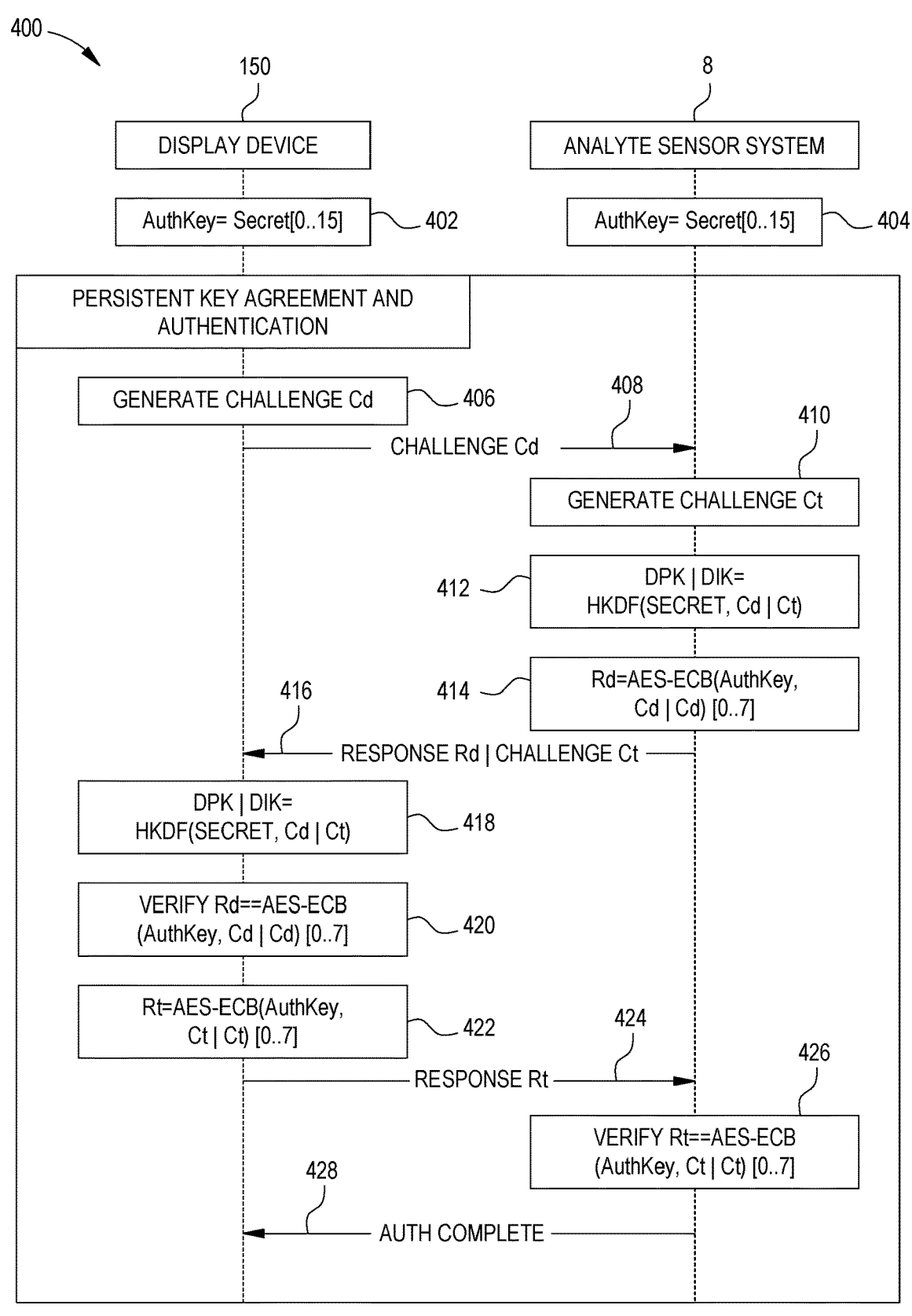
FIG. 4 is a sequence diagram illustrating example operations for performing a persistent key agreement and authentication procedure, according to certain embodiments disclosed herein.

As noted above, the cryptographic key exchange (e.g., EC-JPAKE) produces a 32-byte shared secret which is known at both the display device 150 and the SS 8. Accordingly, as shown in FIG. 4, the persistent key agreement and authentication procedure begins in steps 402 and 404 with the display device 150 and the SS 8, respectively, generating an authentication key (AuthKey). As shown, the AuthKey comprises the first 16 bytes of the 32-byte shared secret generated using EC-JPAKE.

Thereafter, the display device 150 may hash the AuthKey with a random number to generate a display challenge (Cd) in step 406. The display device 150 then sends the display challenge (Cd) to the SS 8 in step 408. In step 410, the SS 8 then generates a transmitter challenge (Ct) by hashing the AuthKey with a random number. Thereafter, in step 412, the SS 8 generates a set of persistent keys, including a data protection key (DPK) and a device identification key (DIK), using a hashed message authentication code (HMAC)-based key derivation function (HKDF) (e.g., SHA256). For example, as shown, the HKDF uses, as inputs, the 32-byte shared secret generated using EC-JPAKE and the concatenation of Cd and Ct (e.g., illustrated in FIG. 4 as Cd|Ct). In some embodiments, the DPK may be used by the display device 150 and the SS 8 to generate a session key for encrypting/decrypting data in an application layer of the display device 150 and/or SS 8, as described with respect to FIG. 5, below. Additionally, the DIK may be used as an identifier to identify the display device 150 and/or SS 8, as described with respect to FIG. 5, below.

In step 414, the SS 8 then generates a challenge response (Rd), for example, in response to the display challenge (Cd) received from the display device 150. The challenge response (Rd) may be generated by the SS 8 based on an Advanced Encryption Standard Electronic Code Book (AES-ECB) using, as inputs, the 16-byte AuthKey and the concatenation of Cd and Cd (e.g., the display challenge (Cd) concatenated with itself or Cd|Cd). In some embodiments, the challenge response (Rd) may comprise the first 8 bytes (e.g., [0 . . . 7]) of the AES-ECB. Thereafter, in step 416, the SS 8 sends the challenge response (Rd) concatenated with the transmitter challenge (Ct) to the display device 150. In some embodiments, challenge response (Rd) and the transmitter challenge (Ct) may be sent in separate messages to the display device 150.

As shown in step 418, the display device 150 may then separately generate the DPK and the DIK by using an HKDF (e.g., SHA256). For example, as shown, the HKDF uses as inputs the 32-byte shared secret generated from EC-JPAKE and the concatenation of the display challenge (Cd) and transmitter challenge (Ct) (e.g., Cd|Ct) received from the SS 8. The display device 150, thereafter, locally generates the challenge response (Rd) in the same manner as was used by the SS 8, as shown in step 420. For example, as shown, the display device 150 locally generates the challenge response (Rd) based on AES-ECB using, as inputs, the 16-byte AuthKey and the concatenation of Cd and Cd (Cd|Cd). In some embodiments, the challenge response (Rd) may comprise the first 8 bytes (e.g., [0 . . . 7]) of the AES-ECB. After locally generating the challenge response (Rd), the display device 150 verifies that the challenge response (Rd) received from the SS 8 matches the challenge response (Rd) locally generated by the display device 150.

When the challenge response (Rd) received from the SS 8 matches the challenge response (Rd) locally generated by the display device 150, the display device 150 then generates a second challenge response (Rt) in response to the transmitter challenge (Ct), as shown in step 422. The second challenge response (Rt) may be generated based on an AES-ECB using, as inputs, the 16-byte AuthKey and a concatenation of Ct and Ct (e.g., the transmitter challenge (Ct) concatenated with itself or Ct|Ct). As shown, second challenge response (Rt) may comprise the first 8 bytes of the AES-ECB. Thereafter, in step 424, the display device 150 sends the second challenge response (Rt) to the SS 8.

In step 426, the SS 8, thereafter, locally generates the second challenge response (Rt) in the same manner as was used by the display device. For example, the SS 8 locally generates the second challenge response (Rt) based on an AES-ECB using, as inputs, the 16-byte AuthKey and a concatenation of Ct and Ct (e.g., the transmitter challenge (Ct) concatenated with itself or Ct|Ct). As shown, the second challenge response (Rt) locally generated by the SS 8 may comprise the first 8 bytes of the AES-ECB. The SS 8 may then verify that the second challenge response (Rt) received from the display device 150 matches the second challenge response (Rt) locally generated by the SS 8.

In step 428, when the second challenge response (Rt) received from the display device 150 matches the second challenge response (Rt) locally generated by the SS 8, the SS 8 transmits an Authentication Complete message to the display device 150. The Authentication Complete message may indicate to the display device 150 that the shared secret separately generated by each of the display device 150 and the SS 8 (e.g., as part of the EC-JPAKE procedure described above) is the same. In such cases, the DIK and DPK generated in steps 412 and 418 may be considered valid, and may be able to be used for device identification and the generation of a session key for ALE encryption/decryption, as described below with respect to the device identification and session key agreement procedure illustrated in FIG. 5.

Device Identification and Session Key Agreement

After persistent key agreement and authentication procedure, the display device 150 and SS 8 may perform a device identification and session key agreement procedure, as shown in step 312 of FIG. 3. As noted above, the device identification and session key agreement procedure may be used to generate a session key for ALE encryption/decryption. Additionally, the session key may be used for forward secrecy and to allow for recovering from an encryption/decryption failure due to loss of synchronization in packet counter values. In other words, the session key may be used to quickly re-authenticate and encrypt communication between the display device and SS 8 in the event of an encryption/decryption failure. Additionally, the device identification and session key agreement procedure allows the SS 8 to resolve an identity of the display device 150 by searching for a matching identity among (previously) known display devices.

Figure 5:
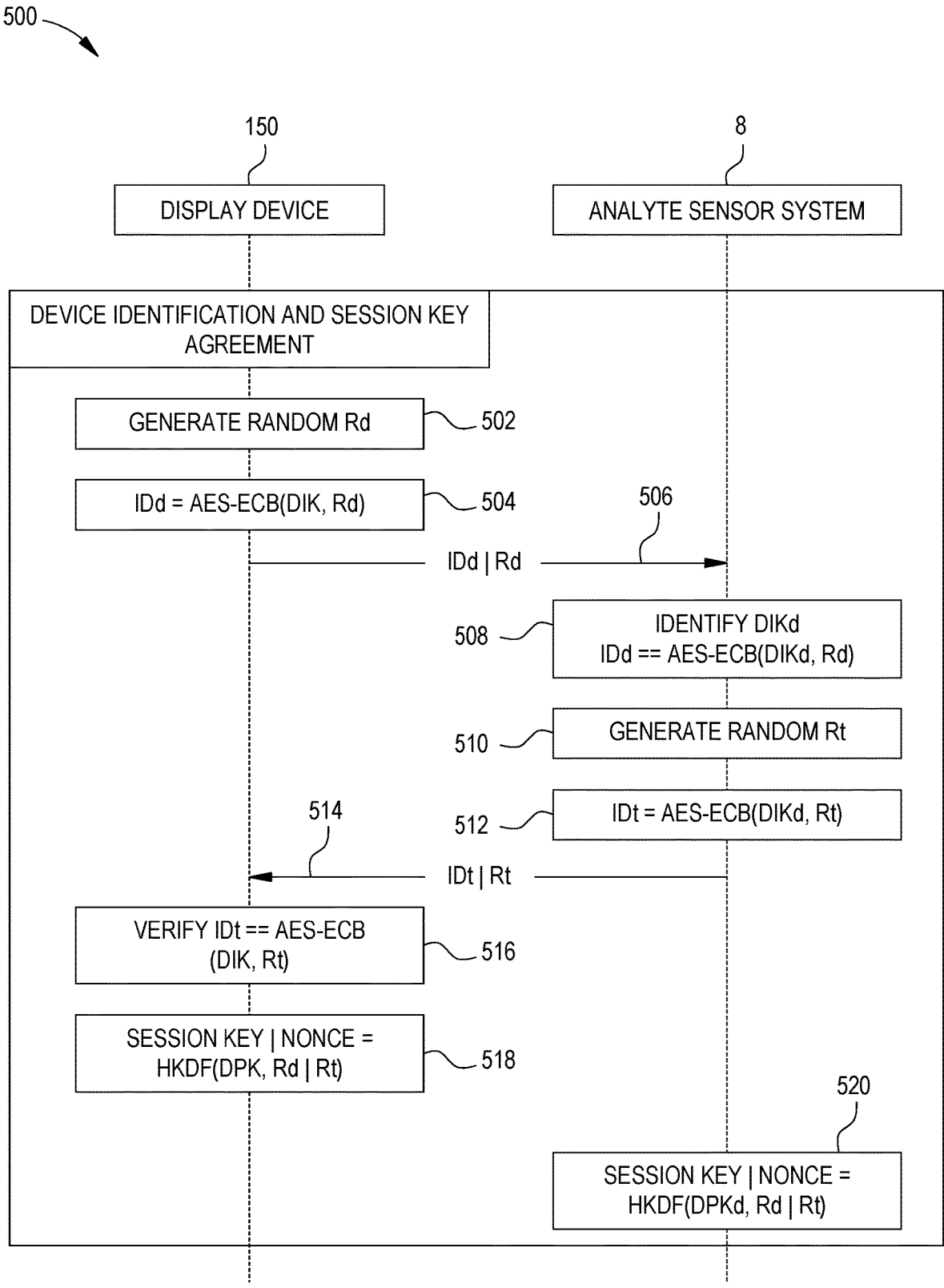
FIG. 5 is a sequence diagram illustrating example operations for performing device identification and session key agreement procedure, according to certain embodiments disclosed herein.
Figure 7:
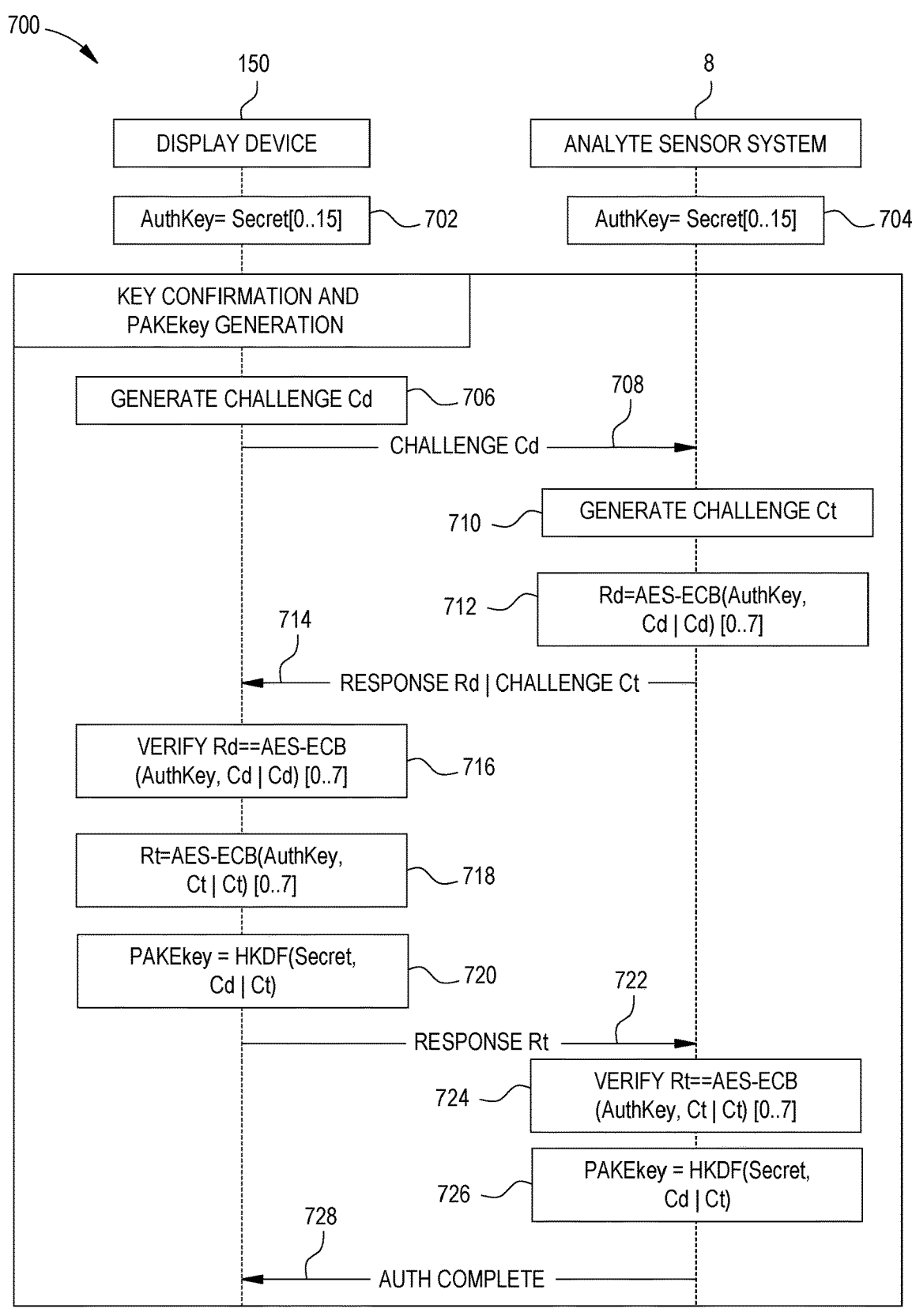
FIG. 7 is a sequence diagram illustrating example operations for performing an explicit key agreement and PAKEkey generation procedure, according to certain embodiments disclosed herein.

FIG. 5 illustrates example operations 500 that may be performed by the SS 8 (e.g., the sensor electronics module 12 of the SS 8) and the display device 150 when performing the device identification and session key agreement procedure described in step 312 in FIG. 3. As shown, operations 500 begin in step 502 with the display device 150 generating a first random number (Rd). It should be noted that this first random number (Rd) is different from, and should not be confused with, the challenge response (Rd) described above in FIG. 4.

Thereafter, in step 504, the display device 150 generates a first identifier (ID) field (IDd) using an AES-ECB. As shown, the inputs to the AES-ECB used by the display device 150 are the DIK (e.g., generated in step 418 of the persistent key agreement and authentication procedure of FIG. 4) and the first random number (Rd). In some embodiments, the first ID field (IDd) may comprise 3-bytes. As shown in step 506, the display device 150 may then send first ID field (IDd) and the first random number (Rd) to the SS 8.

Thereafter, the SS 8 locally generates the first ID field (IDd) using the first random number (Rd) and a DIK selected from a stored list of known DIKs associated with display devices that the SS 8 has previously communicated with or that the SS 8 has been pre-programmed with. For example, the SS 8 may select a first DIK associated with a display device (e.g., DIKd) from the list of known DIKs in combination with the first random number Rd received from the display device 150. The SS 8 may then use the selected first DIK and the first random number (Rd) to locally generate the first ID field (IDd) based on an AES-ECB. The SS 8 may then verify whether the first ID field (IDd) locally generated by the SS 8 matches the first ID field (IDd) received from the display device 150. If, based on the verification, the first ID field (IDd) locally generated by the SS 8 does not match the first ID field (IDd) received from the display device 150, the SS 8 may try a second DIKd associated with another display device from the list of known DIKs in combination with the first random number Rd, and so on.

As shown, when the first ID field (IDd) locally generated by the SS 8 matches the first ID field (IDd) received from the display device 150, the SS 8 then generates a second random number (Rt), as shown in step 510. It should be noted that the second random number (Rt) is different from, and should not be confused with, the challenge response (Rt) described above with respect to FIG. 4. Thereafter, in step 512, the SS 8 then generates a second ID field (IDt) using AES-ECB. As shown, the inputs to the AES-ECB used by the SS 8 are the DIKd (e.g., corresponding to the first ID field (IDd) locally generated by the SS 8 that matches the first ID field (IDd) received from the display device 150) and the second random number (Rt). Thereafter, as shown in step 514, the SS 8 sends second ID field (IDt) and the second random number (Rt) to the display device 150.

Thereafter, in step 516, prior to generating a session key, the display device 150 first verifies that the second ID field (IDt) received from the SS 8 matches a second ID field (IDt) locally generated by the display device 150 based on the DIK of the display device 150. For example, as shown, the display device 150 locally generates the second ID field (IDt) based on an AES-ECB using the DIK of the display device 150 and the second random number (Rt) received from the SS 8.

When the second ID field (IDt) received from the SS 8 matches that second ID field (IDt) locally generated by the display device 150, the display device 150 then proceeds to generate a session key and a nonce, as shown in step 518. The session key and nonce may be generated based on an HKDF using, as inputs, the DPK of the display device 150 (e.g., corresponding to the DIK of the display device 150 generated in step 418 of the persistent key agreement and authentication procedure of FIG. 4) and a concatenation of the first random number (Rd) generated by the display device 150 and the second random number (Rt) generated by the SS 8 (e.g., Rd|Rt). Similarly, as shown in step 520, the SS 8 also locally generates the session key and nonce in a similar manner as the display device based on an HKDF and using the inputs DPKd corresponding to the identified display device 150 (e.g., determined in step 508) and the concatenation of the first random number (Rd) generated by the display device 150 and the second random number (Rt) generated by the SS 8.

In some embodiments, once the session key has been established in step 518 of FIG. 5 between the display device 150 and SS 8, any attempt at performing the persistent key agreement and authentication procedure illustrated in FIG. 4 may be rejected during a same session or connection. In some embodiments, two communication intervals may need to be skipped by the SS 8 in order to perform the persistent key agreement and authentication procedure illustrated in FIG. 4 again (e.g., unless a BLE address of the SS 8 is resolvable). In some embodiments, once the session key has been established, any communication of data between the display device 150 and the SS 8 may be ALE encrypted, as explained below.

Second Example ALE Setup Procedure

Figure 6:
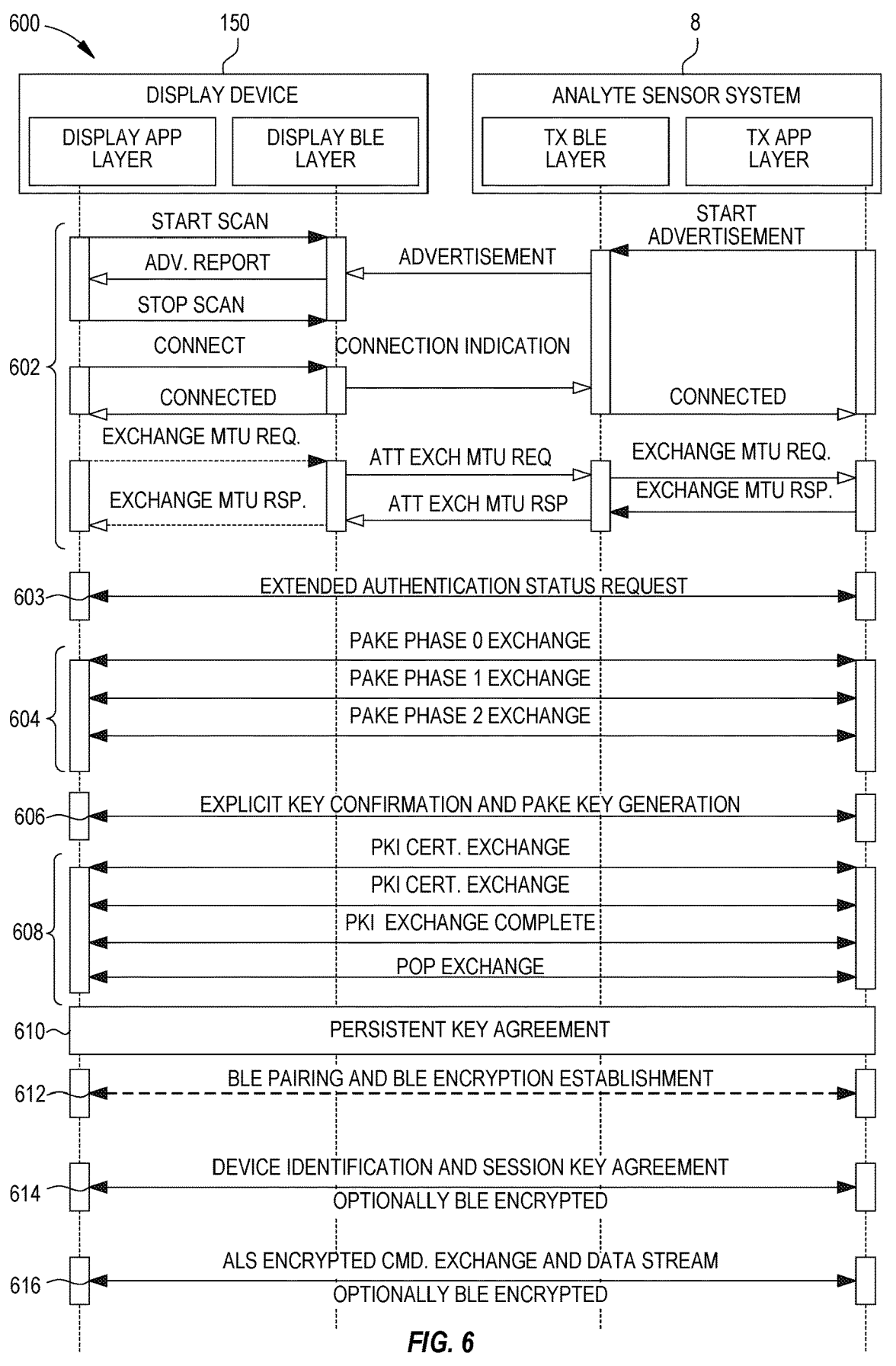

FIG. 6 is a sequence diagram illustrating additional example operations of an example ALE setup procedure 600 that may be performed by the SS 8 and the display device 150, according to certain embodiments described herein.

The ALE setup procedure 600 may be performed by the SS 8 and display device 150 to generate a session key for ALE encryption. In some embodiments, the session key may be generated using security keys generated based on the patient-centric authentication procedure (e.g., PAKE) and the device-centric authentication procedure (e.g., PKI certificate exchange procedure) described above.

For example, as will be described in greater detail below, the operations of the example ALE setup procedure 600 may involve using a shared secret generated based on EC-JPAKE to generate an intermediate key, herein referred to as a PAKEkey. Thereafter, a set of persistent keys may be generated based on the intermediate PAKEkey as well as a PKI public key and a PKI private key. The set of persistent keys may then be used to generate a session key for ALE encryption.

Taking into account security keys generated based on both the patient-centric authentication procedure and the device-centric authentication procedure when generating the session key for ALE encryption may provide for better security and more robust protection against security breaches (e.g., MITM attacks, unauthorized co-located applications on the display device 150 communicating with the SS 8, etc.).

It should be appreciated that one or more of the operations of the ALE setup procedure 600 may be performed by one or more components of the SS 8, such as the sensor electronics module 12, including the one or more processors 11 and/or one or more memories 14. Similarly, one or more of the operations of the ALE setup procedure 600 may also be performed by one or more components of the display device 150, such as the one or more processors 126, the one or more memories 127, and/or the transceiver 129 of the connectivity interface 128. Additionally or alternatively, one or more of the operations of the ALE setup procedure 600 may also be performed by one or more components of the partner devices, such as one or more processors, one or more memories, and/or transceivers of connectivity interface included within the one or more partner devices.

As shown, the example operations begin in step 602 with the SS 8 and the display device 150 performing a scanning and advertising procedure to allow the SS 8 and the display device 150 to discover each other and establish a connection, such as a Bluetooth or Bluetooth Low Energy (BLE) connection. The operations of the scanning and advertising procedure shown in step 602 of FIG. 6 are similar to those of the scanning and advertising procedure shown in step 302 of FIG. 3 and described above.

Thereafter, as shown in step 603, an extended authentication status request procedure may be performed. During the extended authentication status request procedure, the display device 150 may determine that the SS 8 is capable of ALE encryption based on information received from the SS 8, for example, during scanning and advertising procedure in step 602. Thereafter, in some embodiments, if the display device 150 is also capable of ALE encryption, the display device 150 may transmit an extended authentication status request to the SS 8 indicating the capability of the display device 150 for ALE encryption. In some embodiments, failing to send the extended authentication status request would result in the SS 8 assuming the display device 150 intends to operate in a non-ALE communication mode. In some embodiments, when the display device 150 is a smart phone and the ALE setup procedure 600 is being performed by an application executing on the smart phone, the display device 150, via the application executing on the display device 150, may be required to transmit the extended authentication status request to the SS 8 to indicate that the display device 150 is capable of ALE encryption. In some embodiments, if the application executing on the display device 150 is a version of the application that does not support ALE encryption, a user of the display device 150 may be required to update the application to a current version that supports ALE encryption prior to being able to establish a connection between the SS 8 and the display device 150.

Thereafter, as shown in step 604, the SS 8 and display device 150 engage in a cryptographic key exchange. The cryptographic key exchange may involve executing a cryptographic key exchange algorithm, such as EC-JPAKE, to establish a 32-byte shared secret. In certain other embodiments, the cryptographic key exchange algorithm may include a DH key exchange algorithm, ECDH, etc. The operations of the cryptographic key exchange shown in step 604 of FIG. 6 are similar to those of the cryptographic key exchange shown in step 304 of FIG. 3 and described above.

Thereafter, once the shared secret has been generated, the SS 8 and display device 150 may perform a key confirmation and PAKEkey generation procedure, as shown in step 606 in FIG. 6. In some embodiments, key confirmation during the key confirmation and PAKEkey generation procedure may be performed, for example, explicitly or implicitly. The SS 8 and display device 150 may perform the key confirmation and PAKEkey generation procedure to authenticate the shared key produced/generated at each of the SS 8 and display device 150, ensuring that the same shared secret was generated at both the SS 8 and display device 150. Additionally, the SS 8 and display device 150 may perform the key confirmation and PAKEkey generation procedure to generate an intermediate PAKEkey that may be used later to generate a session key for ALE encryption. Additional details regarding the persistent key agreement and authentication procedure performed in step 606 of FIG. 6 will be described with respect to FIG. 7.

Thereafter, as shown in step 608, the SS 8 and display device 150 perform a PKI certification exchange procedure to generate respective PKI key-pairs, including a PKI public key and a PKI private key, for the display device 150 and the SS 8. For example, a first PKI key-pair may be generated for the display device 150, including a PKI private key for the display device 150 (e.g., prvKd) and a PKI public key for the display device 150 (e.g., pubKd). Similarly, second PKI key-pair may be generated for the SS 8, including PKI private key for the SS 8 (e.g., prvKt) and a PKI public key for the SS 8 (e.g., pubKt). Additional details regarding the PKI certification exchange procedure shown in step 608 of FIG. 6 are described above with respect to step 308 illustrated in FIG. 3.

Thereafter, the SS 8 and display device 150 may each perform a persistent key agreement procedure in step 610 to generate a respective set of persistent keys, each including DPK and a DIK. In some embodiments, the DPK may be used by the display device 150 and the SS 8 to generate a session key for encrypting/decrypting data in an application layer of the display device 150 and/or SS 8, as described with respect to FIG. 8, below. Additionally, the DIK may be used as an identifier to identify the display device 150 and/or SS 8, as described with respect to FIG. 8, below. In some embodiments, the display device 150 and SS 8 may each generate respective set of persistent keys based on (1) the PKI public and private keys and (2) the PAKEkey. For example, the display device 150 and/or SS 8 may generate a first set of persistent keys (e.g., DPKd|DIKd) corresponding to the display device 150 according to Equation 1 and a second set of persistent keys (e.g., DPKt|DIKt) corresponding to the SS 8 according to Equation 2.

$$DPKd|DIKd=HKDF(ECDH(prvKd,pubKt),PAKEkey, \\ NULL) \qquad (1)$$

$$DPKt|DIKt=HKDF(ECDH(prvKt,pubKd),PAKEkey, \\ NULL) \qquad (2)$$

As shown, to generate the first set of persistent keys for the display device 150 (e.g., DPKd|DIKd), the display device 150 may first perform ECDH using the PKI private key for the display device 150 (e.g., prvKd) and the PKI public key for the SS 8 (e.g., pubKt). Thereafter, the result of ECDH may be used as an input key to HKDF (e.g., using SHA256 as the hash algorithm) and the PAKEkey may be used as an input salt to HKDF. Additionally, an input information field for HKDF may be set to NULL. Similarly, to generate the second set of persistent keys for the SS 8 (e.g., DPKt|DIKt), the SS 8 may first perform ECDH using the PKI private key for the SS 8 (e.g., prvKt) and the PKI public key for the display device 150 (e.g., pubKd). Thereafter, the result of ECDH may be used as an input key to HKDF (e.g., using SHA256 as the hash algorithm) and the PAKEkey may be used as an input salt to HKDF. Additionally, an input information field for HKDF may be set to NULL.

Thereafter, as shown in step 612, the SS 8 and display device 150 may optionally engage in a BLE paring and BLE encryption establishment procedure to generate one or more BLE security keys that may be used by the SS 8 and display device 150 for encrypting data at a lower protocol layer or BLE layer (e.g., host layer 208 and/or controller layer 210). In some embodiments, encryption of the data (e.g., blood glucose values determined by the SS 8) at the lower protocol layer using the BLE security key is performed in addition to application layer encryption performed on the data at the application layer using an application-layer-based session key established between the SS 8 and display device 150, as described below with respect to step 614 in FIG. 6.

For example, as shown in step 614, the SS 8 and display device 150 may perform a device identification and session key agreement procedure, using the first and second sets of persistent keys generated in step 610. The device identification and session key agreement procedure allows the SS 8 to resolve an identity of the display device 150 by searching for a matching identity among (previously) known display devices 120, for example, based on DIKd. Additionally, the device identification and session key agreement procedure may be used to generate a session key (e.g., based on DIKd) for forward secrecy and to allow for recovering from an encryption/decryption failure due to loss of synchronization in packet counter values. In other words, the session key may be used to quickly re-authenticate and encrypt communication between the display device 150 and SS 8 in the event of an encryption/decryption failure.

In some embodiments, as will be described, the session key may be used for application layer encryption to encrypt data (e.g., blood glucose values and/or other analyte values) at the application layer of the SS 8 and/or display device 150. As noted above, the encryption of data at the application layer may be performed in addition to encryption of the data at the lower protocol layer (e.g., BLE layer) using the BLE security key. Additional details regarding the device identification and session key agreement procedure performed in step 614 of FIG. 6 will be described with respect to FIG. 8.

Thereafter, as shown in step 616 of FIG. 6, the SS 8 and display device 150 may engage in routine communication of ALE-encrypted commands and data. For example, in some embodiments, data for transmission by the SS 8 (e.g., blood glucose values) may first be encrypted at an application layer of the SS 8 based on the session key generated in the device identification and session key agreement procedure, for example, to generate ALE-encrypted data. Thereafter, the ALE-encrypted data may then be provided to a lower protocol layer of the SS 8 (e.g., the host layer 208 and/or controller layer 210). In some embodiments, the ALE-encrypted data may be encrypted again by the lower protocol layer of the SS 8 using one or more security keys, such as the BLE security key discussed above, to generate two-level encrypted data (e.g., twice-encrypted data).

Thereafter, the two-level encrypted data may then be transmitted to the display device 150. The display device 150 may then perform complementary decryption operations to decrypt the two-level encrypted data. For example, a lower protocol layer (e.g., BLE layer) may first decrypt the data using the BLE security key to obtain the ALE-encrypted data. Thereafter, the lower protocol layer may provide the ALE-encrypted data to an application layer of the display device 150. An authorized application in the application layer of the display device 150 may then use the session key generated during the device identification and session key agreement procedure performed in step 614 of FIG. 6 to decrypt the ALE-encrypted data for a second time to recover the data generated by the application layer of the SS 8 (e.g., the blood glucose values and/or other analyte values).

Key Confirmation and PAKEkey Generation

As noted above, FIG. 7 illustrates example operations 700 that may be performed by the SS 8 (e.g., the sensor electronics module 12 of the SS 8) and the display device 150 when performing the key confirmation and PAKEkey generation procedure described in step 606 in FIG. 6.

As noted above, the cryptographic key exchange (e.g., EC-JPAKE) produces a 32-byte shared secret which is known at both the display device 150 and the SS 8. Accordingly, as shown in FIG. 4, the key confirmation and PAKEkey generation procedure begins in steps 702 and 704 with the display device 150 and the SS 8, respectively, generating an authentication key (AuthKey). As shown, the AuthKey comprises the first 16 bytes of the 32-byte shared secret generated using EC-JPAKE.

Thereafter, the display device 150 may hash the AuthKey with a random number to generate a display challenge (Cd) in step 706. The display device 150 then sends the display challenge (Cd) to the SS 8 in step 708. In step 710, the SS 8 then generates a transmitter challenge (Ct) by hashing the AuthKey with a random number.

In step 712, the SS 8 then generates a challenge response (Rd), for example, in response to the display challenge (Cd) received from the display device 150. The challenge response (Rd) may be generated by the SS 8 based on an Advanced Encryption Standard Electronic Code Book (AES-ECB) using, as inputs, the 16-byte AuthKey and the concatenation of Cd and Cd (e.g., the display challenge (Cd) concatenated with itself or Cd|Cd). In some embodiments, the challenge response (Rd) may comprise the first 8 bytes (e.g., [0 . . . 7]) of the AES-ECB. It should be noted that, while step 710 is illustrated as being performed before step 712, these steps may be performed interchangeably. As such, in some embodiments, step 712 may be performed before 710.

Thereafter, in step 714, the SS 8 sends the challenge response (Rd) concatenated with the transmitter challenge (Ct) to the display device 150. In some embodiments, challenge response (Rd) and the transmitter challenge (Ct) may be sent in separate messages to the display device 150.

The display device 150, thereafter, locally generates the challenge response (Rd) in the same manner as was used by the SS 8, as shown in step 716. For example, as shown, the display device 150 locally generates the challenge response (Rd) based on an Advanced Encryption Standard Electronic Code Book (AES-ECB) using, as inputs, the 16-byte Auth-Key and the concatenation of Cd and Cd (Cd|Cd). In some embodiments, the challenge response (Rd) may comprise the first 8 bytes (e.g., [0 . . . 7]) of the AES-ECB. After locally generating the challenge response (Rd), the display device 150 verifies that the challenge response (Rd) received from the SS 8 matches the challenge response (Rd) locally generated by the display device 150.

When the challenge response (Rd) received from the SS 8 matches the challenge response (Rd) locally generated by the display device 150, the display device 150 then generates a second challenge response (Rt) in response to the transmitter challenge (Ct), as shown in step 718. The second challenge response (Rt) may be generated based on an AES-ECB using, as inputs, the 16-byte AuthKey and a concatenation of Ct and Ct (e.g., the transmitter challenge (Ct) concatenated with itself or Ct|Ct). As shown, second challenge response (Rt) may comprise the first 8 bytes (e.g., [0 . . . 7]) of the AES-ECB.

Additionally, as shown in step 720, when the challenge response (Rd) received from the SS 8 matches the challenge response (Rd) locally generated by the display device 150, the display device 150 then generates an intermediate PAKEkey. As shown, the PAKEkey may be generated using HKDF (e.g., using SHA256 as the hash algorithm). For example, as shown, the HKDF uses, as inputs, the 32-byte shared secret generated using EC-JPAKE and the concatenation of Cd and Ct (e.g., illustrated in FIG. 7 as Cd|Ct).

Thereafter, in step 722, the display device 150 sends the second challenge response (Rt) to the SS 8. It should be noted that, while step 720 is illustrated as being performed before step 722, these steps may be performed interchangeably. As such, in some embodiments, step 722 may be performed before 720.

In step 724, the SS 8, thereafter, locally generates the second challenge response (Rt) in the same manner as was used by the display device. For example, the SS 8 locally generates the second challenge response (Rt) based on an AES-ECB using, as inputs, the 16-byte AuthKey and a concatenation of Ct and Ct (e.g., the transmitter challenge (Ct) concatenated with itself or Ct|Ct). As shown, the second challenge response (Rt) locally generated by the SS 8 may comprise the first 8 bytes (e.g., [0 . . . 7]) of the AES-ECB. The SS 8 may then verify that the second challenge response (Rt) received from the display device 150 matches the second challenge response (Rt) locally generated by the SS 8.

As shown in step 726, when the second challenge response (Rt) received from the display device 150 matches the second challenge response (Rt) locally generated by the SS 8, the SS 8 then generates the intermediate PAKEkey in a same manner as is used by the display device 150. For example, as shown, the PAKEkey may be generated by the SS 8 using HKDF (e.g., using SHA256 as the hash algorithm). As noted above, HKDF uses, as inputs, the 32-byte shared secret generated using EC-JPAKE and the concatenation of Cd and Ct (e.g., illustrated in FIG. 7 as Cd|Ct).

In step 728, after the PAKEkey is generated by the SS 8, the SS 8 transmits an Authentication Complete message to the display device 150. The Authentication Complete message may indicate to the display device 150 that the shared secret separately generated by each of the display device 150 and the SS 8 (e.g., as part of the EC-JPAKE procedure described above) is the same. In such cases, the PAKEkey generated in steps 720 and 726 may be considered valid, and may be used by the display device 150 and SS 8 to generate the first set of persistent keys and the second set of persistent keys, respectively, as described with respect to step 610 in FIG. 6.

Device Identification and Session Key Agreement Based on PAKEkey

As noted above, the display device 150 and SS 8 may use the PAKEkey, along with the private and public keys of the first PKI key-pair and the second PKI key-pair, to generate the first set of persistent keys (e.g., DPKd|DIKd) and the second set of persistent keys (e.g., DPKt|DIKt), as described with respect to step 610 in FIG. 6. The display device 150 and SS 8 may then perform the device identification and session key agreement procedure, as shown in step 614 of FIG. 6 based, at least on, the first set of persistent keys (e.g., DPKd|DIKd), to generate a session key for ALE encryption. As noted above, the session key may be used for forward secrecy and for recovering from an encryption/decryption failure due to loss of synchronization in packet counter values. In other words, the session key may be used to quickly re-authenticate and encrypt communication between the display device and SS 8 in the event of an encryption/decryption failure. Additionally, the device identification and session key agreement procedure allows the SS 8 to resolve an identity of the display device 150 by searching for a matching identity among (previously) known display devices.

In some embodiments, the device identification and session key agreement procedure may be performed by the display device 150 and SS 8 periodically throughout an operating session of the SS 8. For example, in some embodiments, the device identification and session key agreement procedure may be performed by the display device 150 and SS 8 at predetermined times, (e.g., every minute or less, five minutes or ten minutes). In some embodiments, the device identification and session key agreement procedure may be performed by the display device 150 and SS 8 upon reestablishment of a connection between the display device 150 and SS 8. For example, after pairing with each other, there may be some scenarios in which a user of the SS 8 sets down and walks away from the display device 150 such that a connection (e.g., a Bluetooth-based connection) between the display device 150 and the SS 8 fails. When the user of the SS 8 inevitably returns to an area of the display device 150, the display device 150 and SS 8 may reestablish the connection and may re-perform the device identification and session key agreement procedure to reestablish a session key for ALE encryption.

Figure 8:
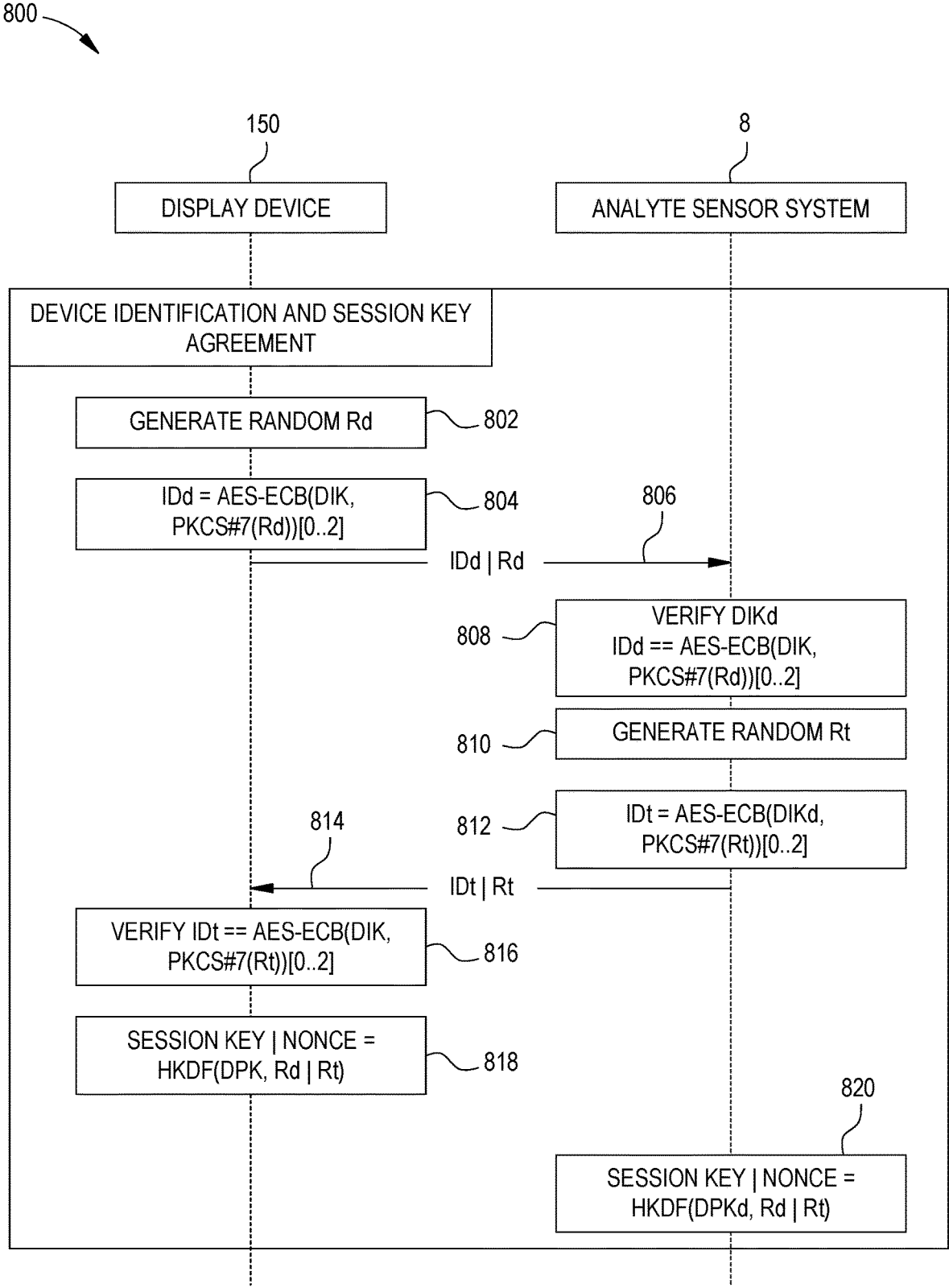
FIG. 8 is a sequence diagram illustrating additional example operations for performing device identification and session key agreement procedure, according to certain embodiments disclosed herein.

FIG. 8 illustrates example operations 800 that may be performed by the SS 8 (e.g., the sensor electronics module 12 of the SS 8) and the display device 150 when performing the device identification and session key agreement procedure described in step 614 in FIG. 6. As shown, operations 800 begin in step 802 with the display device 150 generating a first random number (Rd). It should be appreciated that that the first random number (Rd) is different from the challenge response (Rd) described above in FIG. 7.

Thereafter, in step 804, the display device 150 generates a first identifier (ID) field (IDd) using an AES-ECB. As shown, the inputs to the AES-ECB used by the display device 150 are the DIKd (e.g., generated in step 610 of the persistent key agreement procedure of FIG. 6) and the first random number (Rd) padded using a cryptography standard, such Public-Key Cryptography Standards (PKCS) number 7 (PKCS #7). In some embodiments, the first ID field (IDd) may comprise 3-bytes (e.g., [0 . . . 2]). As shown in step 806, the display device 150 may then send first ID field (IDd) and the first random number (Rd) to the SS 8.

Thereafter, the SS 8 locally generates the first ID field (IDd) using the first random number (Rd) and a DIK selected from a stored list of known DIKs associated with display devices that the SS 8 has previously communicated with or that the SS 8 has been pre-programmed with. For example, the SS 8 may select a first DIK associated with a display device (e.g., DIKd) from the list of known DIKs in combination with the first random number Rd received from the display device 150. The SS 8 may then use the selected first DIK and the first random number (Rd) to locally generate the first ID field (IDd) based on AES-ECB. The SS 8 may then verify whether the first ID field (IDd) locally generated by the SS 8 matches the first ID field (IDd) received from the display device 150. If, based on the verification, the first ID field (IDd) locally generated by the SS 8 does not match the first ID field (IDd) received from the display device 150, the SS 8 may try a second DIKd associated with another display device from the list of known DIKs in combination with the first random number Rd, and so on.

As shown, when the first ID field (IDd) locally generated by the SS 8 matches the first ID field (IDd) received from the display device 150, the SS 8 then generates a second random number (Rt), as shown in step 810. It should be noted that the second random number (Rt) is different from, and should not be confused with, the challenge response (Rt) described above with respect to FIG. 7. Thereafter, in step 812, the SS 8 then generates a second ID field (IDt) using AES-ECB. As shown, the inputs to the AES-ECB used by the SS 8 are the DIKd (e.g., corresponding to the first ID field (IDd) locally generated by the SS 8 that matches the first ID field (IDd) received from the display device 150) and the second random number (Rt) padded using PKCS #7. Thereafter, as shown in step 814, the SS 8 sends second ID field (IDt) and the second random number (Rt) to the display device 150.

Thereafter, in step 816, prior to generating a session key, the display device 150 first verifies that the second ID field (IDt) received from the SS 8 matches a second ID field (IDt) locally generated by the display device 150 based on the DIK of the display device 150. For example, as shown, the display device 150 locally generates the second ID field (IDt) based on an AES-ECB using DIKd of the display device 150 (e.g., generated in step 610 of FIG. 6) and the second random number (Rt) received from the SS 8.

When the second ID field (IDt) received from the SS 8 matches that second ID field (IDt) locally generated by the display device 150, the display device 150 then proceeds to generate a session key and a nonce, as shown in step 818. The session key and nonce may be generated based on an HKDF using, as inputs, the DPK (e.g., DPKd) of the display device 150 (e.g., corresponding to the DIKd of the display device 150 generated in step 610 of the persistent key agreement and procedure of FIG. 6) and a concatenation of the first random number (Rd) generated by the display device 150 and the second random number (Rt) generated by the SS 8 (e.g., Rd|Rt). Similarly, as shown in step 520, the SS 8 also locally generates the session key and nonce in a similar manner as the display device based on an HKDF and using the inputs DPKd corresponding to the identified display device 150 (e.g., determined in step 808 based on DIKd) and the concatenation of the first random number (Rd) generated by the display device 150 and the second random number (Rt) generated by the SS 8.

In some embodiments, once the session key has been established in steps 818 and 820 of FIG. 8 between the display device 150 and SS 8, any attempt at performing the persistent key agreement procedure illustrated in FIG. 8 may be rejected during a same session or connection. In some embodiments, two communication intervals may need to be skipped by the SS 8 in order to perform the persistent key agreement procedure illustrated in FIG. 8 again (e.g., unless a BLE address of the SS 8 is resolvable). In some embodiments, once the session key has been established, any communication of data between the display device 150 and the SS 8 may be ALE encrypted, as explained below.

Example Operations for ALE-Based Encryption

Once the session key has been generated, the ALE setup procedure is complete. The display device 150 and SS 8 may then use the session key to encrypt a communication channel between the display device 150 and SS 8. For example, the session key may be used by an authorized application on the display device 150 (e.g., analyte sensor application 121 of FIG. 1B) to encrypt communication at an application layer (e.g., application layer 204) transmitted via BLE to the SS 8. Similarly, the session key may be used by an application (e.g., analyte sensor application 18 of FIG. 1B) to encrypt communication at an application layer (e.g., application layer 204) transmitted via BLE to the display device 150. Additionally, the session key may be used by the display device 150 to decrypt data at an application received from the SS 8. Similarly, the session key may be used by the SS 8 to decrypt data at an application received from the display device 150.

As noted above, the encryption performed in the application layer of the display device 150 and/or SS 8 may be performed in addition to optional encryption performed by a lower protocol layer (e.g., host layer 208 and/or controller layer 210) of the display device 150 and/or SS 8 based on, for example, a BLE security key described above. In other words, information or data that is to be transmitted between the display device 150 and SS 8 may first be encrypted in the application layer using the session key generated in steps 518 and 520 of FIG. 5 and/or steps 818 and 820 of FIG. 8. Thereafter, the information or data encrypted in the application layer may then be optionally encrypted based on BLE encryption using a BLE security key generated in step 310 of FIG. 3 or step 612 of FIG. 6. Additional details regarding the encryption and decryption of data by the display device 150 and SS 8 is described with respect to FIG. 9.

Figure 9:
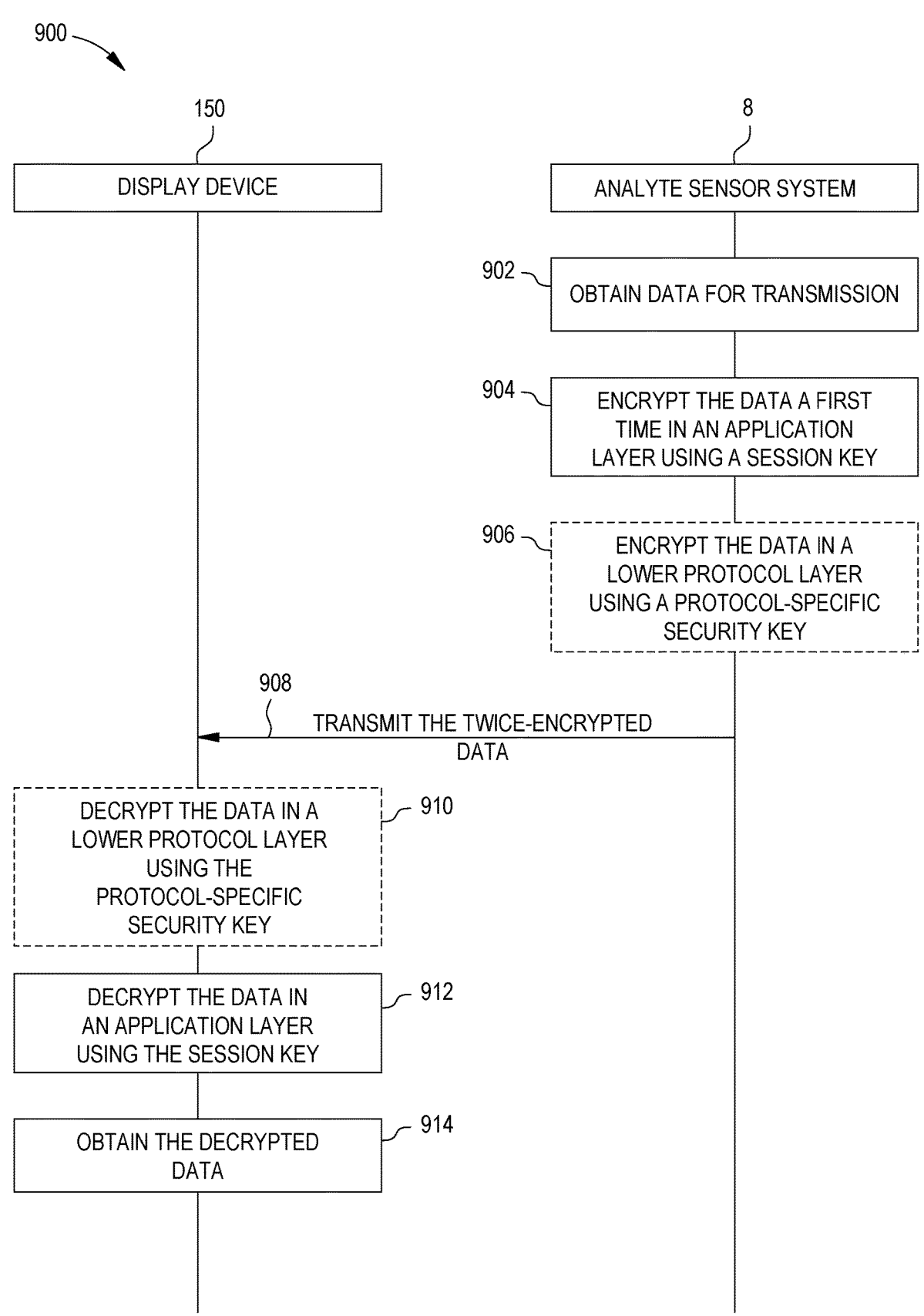
FIG. 9 is a sequence diagram illustrating example operations performed by an analyte sensor system and a display device for ALE-based encryption and decryption of data, according to certain embodiments disclosed herein.

For example, FIG. 9 illustrates example operations 900 for ALE-based encryption and decryption of data. In some embodiments, the operations 900 may be performed by the SS 8 (e.g., the sensor electronics module 12 of the SS 8) and the display device 150 for securely transmitting and receiving analyte data (e.g., blood glucose values or other analyte levels) of a patient.

As shown, operations 900 begin in step 902 with the SS 8 obtaining data for transmission to the display device 150. In some cases, the data may include analyte data, such as blood glucose values or other analyte levels of a patient associated with the SS 8. In some embodiments, the data may be obtained by an application (e.g., analyte sensor application 18 illustrated in FIG. 1B) in an application layer (e.g., application layer 204 illustrated in FIG. 2) of the sensor electronics module 12 of the SS 8 from an analyte sensor (e.g., analyte sensor 10 illustrated in FIG. 1B) operatively coupled (e.g., electrically coupled and/or mechanically coupled, pre-coupling, post-coupling, etc.) to the sensor electronics module 12. Thereafter, as shown in step 904, the SS 8 (e.g., via the analyte sensor application 18) encrypts the data a first time in the application layer of the SS 8 using a session key, such as the session key generated in step 520 of FIG. 5 or step 820 of FIG. 8, to obtain ALE-encrypted data.

Thereafter, the ALE-encrypted data may be provided to a lower protocol layer of the SS 8, such as a Bluetooth or BLE layer of the SS 8 (e.g., host layer 208 and/or controller layer 210). In step 906, the lower protocol layer of the SS 8 may then optionally encrypt the ALE-encrypted data a second time using a protocol-specific security or encryption key (e.g., such as a BLE security key generated in step 310 of FIG. 3 or in step 612 of FIG. 6) to obtain two-level encrypted data (e.g., twice-encrypted data: data that has been ALE-encrypted in the application layer of the SS 8 and BLE-encrypted in the lower protocol layer of SS 8). Thereafter, as shown in step 908, the SS 8 transmits the two-level encrypted data, which may be received by the display device 150.

In step 910, a lower protocol layer of the display device 150 may then optionally decrypt the two-level encrypted data received from the SS 8 a first time using the protocol-specific security key to obtain the ALE-encrypted data. Thereafter, the lower protocol layer of the display device 150 provides the ALE-encrypted data to an authorized application in an application layer (e.g., analyte sensor application 121 of FIG. 1B) of the display device 150. In step 912, the authorized application may then decrypt the ALE-encrypted data (e.g., received from the lower protocol layer of the display device) a second time using the session key generated in step 518 of FIG. 5 or in step 818 of FIG. 8. As shown in step 914, after decrypting the ALE-encrypted data, the display device 150 obtains or recovers the (de-crypted) data (e.g., blood glucose values or other analyte levels) sent by the SS 8. In some embodiments, if decryption fails at the application layer a threshold number of times (e.g., three), a connection to the SS 8 may be disabled.

While FIG. 9 illustrates example operations for transmitting data from the SS 8 to the display device 150, similar complementary operations may be performed for transmitting data or commands from the display device 150 to the SS 8.

Because the data transmitted between the SS 8 and display device 150 is only completely decrypted by an authorized application in the application layer of the display device 150 (and/or SS 8), other unauthorized co-located applications (the co-located application(s) 124 illustrated in FIG. 1B) in the application layer of the display device 150 may not be able to access the data, alleviating the security concerns described above regarding unauthorized co-located applications. Additionally, as previously discussed, the encrypting and decrypting of data at the application layer helps to avoid MITM attacks since, even if a MITM attacker possessed the protocol-specific security key used for encrypting and decrypting the data at the lower protocol layer, the MITM attacker would not possess the session key to be able to encrypt or decrypt the data at the application layer transmitted between the SS 8 and display device 150. Moreover, the display device 150 and SS 8 may be configured to detect whether data communicated between the display device 150 and SS 8 has been encrypted using the session key. If the display device 150 and/or SS 8 detects that the data has not been encrypted using the session key, the display device 150 and/or SS 8 may be configured to discard this data.

Additional Considerations Regarding Use of ALE Encryption

In some embodiments, while ALE encryption should be used by default, there may be scenarios in which ALE may be deactivated and a non-ALE communication mode used for communication between the display device 150 and the SS 8. For example, the non-ALE communication mode may involve relying only on the protocol-specific security key (e.g., Bluetooth or BLE security key) for encrypting the communication between the display device 150 and SS 8. For example, in some embodiments, the non-ALE communication mode may be used in various scenarios, such as when the display device 150 does not support ALE-encryption. In other scenarios, non-ALE communication mode may be used when: (1) a device type associated with the display device 150 is set to "medical," (2) a communication link between the SS 8 and display device 150 is already encrypted using a BLE bond, (3) the SS 8 skips the device identification and session key agreement procedure in step 312 of FIG. 3 and directly accesses protected characteristics, and (4) the SS 8 is not currently operating in an ALE communication mode. In some embodiments, if at least one of the criteria above is not satisfied, ALE may be enforced for communication between the display device 150 and SS 8.

In some embodiments, the SS 8 may determine the device type of the display device 150 by transmitting a query message to the display device 150 requesting the device type of the display device 150. In response to receiving the query message, the display device 150 may transmit a response message indicating at least the device type of the display device 150 (e.g., medical, non-medical, etc.). In some cases, the SS 8 may transmit the query message to the display device 150 at any time after the scanning and advertising procedure in step 302 of FIG. 3 or step 602 of FIG. 6 but before the device identification and session key agreement procedure in step 312 of FIG. 3 or step 614 of FIG. 6.

In some embodiments, whether the non-ALE communication mode will be used may be based on a capability of the display device 150 to perform ALE encryption. For example, if the display device 150 transmits, in step 603 of FIG. 6, the extended authentication status request to the SS 8, the SS 8 may assume that the display device 150 is capable of ALE encryption and may force the display device to perform the ALE setup procedure to generate a session key for ALE encryption. In other words, when the display device 150 is capable of ALE encryption, the display device 150 may be forced to perform the key confirmation and PAKEkey generation procedure in step 606, the persistent key agreement procedure in step 610, and the device identification and session key agreement procedure in step 614.

In some scenarios, when the extended authentication status request transmitted by the display device 150 indicates that the display device 150 is not capable of ALE encryption or when the display device 150 does not transmit the extended authentication status request to the SS 8 (e.g., providing an implicit indication that the display device 150 does not support ALE encryption), the SS 8 may assume that the display device 150 is not capable of ALE encryption and may permit the display device 150, in some embodiments, to operate in a non-ALE communication mode. In some embodiments, however, when the display device 150 indicates that it is not capable of ALE encryption, the SS 8 may verify what the display device 150 has indicated (e.g., that the display device 150 is not capable of ALE encryption) to the SS 8 is accurate. The SS 8 may perform this verification to avoid scenarios in which a display device 150 maliciously tries establish a connection with the SS 8 without ALE encryption when the display device 150 is, in fact, capable of ALE encryption. In some cases, the SS 8 may perform this verification based on PKI certificates received from the display device 150 during the PKI certification exchange procedure in step 608 of FIG. 6.

For example, in some embodiments, when registering with a certificate authority, the display device 150 may be issued one or more PKI certificates that may include an indication of whether the display device 150 is capable of ALE encryption. Once these PKI certificates have been issued, they may not be altered. As such, after the certificate exchange during the PKI certification exchange procedure in step 608 of FIG. 6, the SS 8 may verify that what the display device 150 has indicated regarding its capabilities for ALE encryption are consistent with the one or more PKI certificates of the display device 150. For example, if the display device 150 indicates that it is not capable of ALE encryption while the one or more PKI certificates of the display device 150 indicate that the display device 150 is capable of ALE encryption, then the SS 8 may force the display device to perform the ALE encryption setup procedure, including the key confirmation and PAKEkey generation procedure in step 606, the persistent key agreement procedure in step 610, and the device identification and session key agreement procedure in step 614. If, however, the display device 150 indicates that it is not capable of ALE encryption and the one or more PKI certificates of the display device 150 also indicate that the display device 150 is not capable of ALE encryption, then the SS 8 may permit the display device 150 to communicate with the SS 8 using the non-ALE communication mode.

Figure 10:
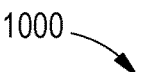
FIG. 10 is a sequence diagram illustrating example operations for deciding whether or not to allow the display device to use a non-ALE communication mode.

FIG. 10 illustrates an example decision flow diagram including operations 1000 that may be performed by the SS 8 to decide whether or not to allow the display device 150 to use a non-ALE communication mode. In some cases, the operations 1000 may be performed during initial connection establishment between the SS 8 and display device 150, such as during the ALE setup procedure 300 or the ALE setup procedure 600. Thereafter, upon subsequent re-connections between the SS 8 and display device 150 (e.g., due to the display device 150 becoming out of range of the SS 8 and subsequently coming back into range of the SS 8), the SS 8 may not be required to re-perform the operations 1000 with respect to the display device 150 as the SS 8 will already know whether or not to permit the display device 150 to communicate using the non-ALE communication mode.

For example, as illustrated at 1002, the SS 8 may obtain information from the display device 150. In some embodiments, the information may include an indication of whether the display device 150 is capable of ALE encryption. In some embodiments, the indication of whether the display device 150 is capable of ALE encryption may be obtained by the SS 8 in an extended authentication status request from the display device 150, for example, in step 603 of FIG. 6. In some embodiments, the information may indicate a device type of the display device 150 (e.g., medical, non-medical, etc.). In some cases, the information may also include one or more PKI certificates received from the display device 150 in step 608 of FIG. 6, for example, that may indicate whether the display device 150 is capable of ALE encryption.

Thereafter, at 1004, the SS 8 may determine whether to permit the display device 150 to use non-ALE communication with the SS 8. In some cases, determining whether to permit the display device 150 to use non-ALE communication may include verifying the information including the indication of whether the display device 150 is capable of ALE encryption. For example, as discussed above, in some embodiments, the SS 8 may compare the indication of whether the display device 150 is capable of ALE encryption obtained by the SS 8 in the extended authentication status request and/or the information indicating the device type of the display device to with the one or more PKI certificates obtained from the display device 150.

In some embodiments, if the display device 150 indicates in the extended authentication status request that the display device 150 is not capable of supporting ALE encryption and if the one or more PKI certificates are consistent with the indication provided in the extended authentication status request, then the SS 8 may decide to permit the display device 150 to use non-ALE communication with the SS 8 (e.g., YES at 1004). In such cases, as shown at 1006, because the display device 150 is permitted to use non-ALE communication, the SS 8 may set up a connection and communicate with the display device 150 using the non-ALE communication mode, for example, in which communications between the SS 8 and display device 150 are not encrypted using ALE encryption. For example, rather than relying on ALE encryption, in the non-ALE communication mode, the SS 8 and display device 150 may instead rely only on the BLE encryption discussed above. Accordingly, because the display device 150 does not support ALE encryption and is permitted to use the non-ALE communication mode, the display device 150 is permitted to not perform the persistent key agreement and authentication procedure in step 306 of FIG. 3 or the device identification and session key agreement procedure in step 312 of FIG. 3. Similarly, because the display device 150 does not support ALE encryption and is permitted to use the non-ALE communication mode, the display device 150 may be permitted to not perform the key confirmation and PAKEkey generation procedure in step 606 of FIG. 6, the persistent key agreement procedure in step 610 of FIG. 6, and the device identification and session key agreement procedure in step 614 of FIG. 6.

If, however, the display device 150 indicates that it is capable of ALE encryption (e.g., the display device 150 is a smart phone and is required to support ALE encryption) or if the indication of the ALE encryption capability of the display device in the extended authentication status request is not consistent with the one or more PKI certificates, then the SS 8 may decide to not permit the display device 150 to use non-ALE communication with the SS 8 (e.g., NO at 1004). In such cases, as shown at 1008, because the display device 150 is not permitted to use non-ALE communication, the SS 8 may set up a connection and communicate with the display device 150 using an ALE communication mode, for example, in which communications between the SS 8 and display device 150 are encrypted using ALE encryption. Accordingly, because the display device 150 is not permitted to use the non-ALE communication mode, the display device 150 may be forced to perform the persistent key agreement and authentication procedure in step 306 of FIG. 3 and the device identification and session key agreement procedure in step 312 of FIG. 3. Similarly, because the display device 150 is not permitted to use the non-ALE communication mode, the display device 150 may be forced to perform the key confirmation and PAKEkey generation procedure in step 606 of FIG. 6, the persistent key agreement procedure in step 610 of FIG. 6, and the device identification and session key agreement procedure in step 614 of FIG. 6.

Example Operations by an Analyte Sensor System

FIG. 11 is a flow diagram illustrating example operations 1100 for transmitting analyte data of a user (e.g., a patient), according to certain embodiments described herein. The operations 1100 may be performed by one or more components of an analyte sensor system, such as the sensor electronics module 12 of the SS 8. For example, in some embodiments, one or more components of the sensor electronics module 12 may be configured to perform operations 1100, such as the SMC 13, the RTC 17, the one or more processors 11, the one or more memories 14, and/or the transceiver (TRX) 16 of the connectivity interface 15 illustrated in FIG. 1B. Additionally, it should be appreciated that operations 1100 are representative of the operations performed by the SS 8 described with respect to the ALE setup procedure 300 of FIG. 3 and the ALE setup procedure 600 of FIG. 6.

Operations 1100 begin in step 1102 with the sensor electronics module obtaining analyte data from an analyte sensor operatively coupled to the sensor electronics module.

In step 1104, the sensor electronics module encrypts, in an application layer of a protocol stack of the sensor electronics module, the analyte data using a session key established between the analyte sensor system and a display device.

In step 1106, the sensor electronics module transmits the encrypted analyte data to the display device.

In some embodiments, operations 1100 further include establishing a shared secret with the display device. In some embodiments, establishing the shared secret with the display device is based on a juggling password authenticated key exchange using elliptic curve cryptography (EC-JPAKE) protocol.

In some embodiments, operations 1100 further include receiving a first challenge message from the display device. In some embodiments, operations 1100 further include generating a second challenge message based, at least in part, on an authentication key derived from the shared secret. In some embodiments, operations 1100 further include generating a first challenge response message based, at least in part, on the authentication key and the first challenge message. In some embodiments, operations 1100 further include transmitting the first challenge response message and the second challenge message to the display device.

In some embodiments, operations 1100 further include generating a data protection key (DPK) and a device identification key (DIK). In some embodiments, the DPK and the DIK are generated based, at least in part, on the shared secret, the first challenge message, and the second challenge message.

In some embodiments, operations 1100 further include generating an intermediate password authenticated key exchange key (PAKEkey) based, at least in part, on the shared secret, the first challenge message, and the second challenge message. In some embodiments, the DPK and DIK are generated based on a public key infrastructure (PKI) private key of the analyte sensor system, a PKI public key of the display device, and the intermediate PAKEkey.

In some embodiments, operations 1100 further include receiving, from the display device, a second challenge response message. In some embodiments, operations 1100 further include generating a third challenge response message based, at least in part, on the authentication key and the second challenge message. In some embodiments, operations 1100 further include verifying that the second challenge response message received from the display device matches the third challenge response message generated by the sensor electronics module. In some embodiments, operations 1100 further include transmitting, based on the verifying, an authentication completion message to the display device.

In some embodiments, operations 1100 further include maintaining a list of device identification keys (DIKs) and corresponding data protection keys (DPKs) associated with one or more display devices. In some embodiments, operations 1100 further include receiving a first identification field and a first random number from a display device of the one or more display devices. In some embodiments, operations 1100 further include selecting, from the list of DIKs, a DIK associated with the display device. In some embodiments, operations 1100 further include generating a second identification field based on the selected DIK associated with the display device and the random number received form the display device. In some embodiments, operations 1100 further include verifying that the first identification field received from the display device matches the second identification field generated by the sensor electronics module.

In some embodiments, the first identification field and the second identification field are padded based on a cryptography standard.

In some embodiments, operations 1100 further include generating, based on the verifying, a second random number. In some embodiments, operations 1100 further include generating a third identification field based on the selected DIK associated with the display device and a second random number. In some embodiments, operations 1100 further include transmitting the third identification field and the second random number to the display device. In some embodiments, operations 1100 further include generating the session key and a nonce based on the first random number, the second random number, and a DPK corresponding to the selected DIK associated with the display device.

In some embodiments, the third identification field is padded based on a cryptography standard.

In some embodiments, operations 1100 further include encrypting, in a lower layer of the protocol stack of the sensor electronics module, the encrypted analyte data using a protocol-specific security key established between the analyte sensor system and a display device to obtain two-level encrypted analyte data. In such embodiments, transmitting the encrypted analyte data to the display device in step 1106 comprises transmitting the two-level encrypted analyte data to the display device.

Example Operations by a Display Device

Figure 12:
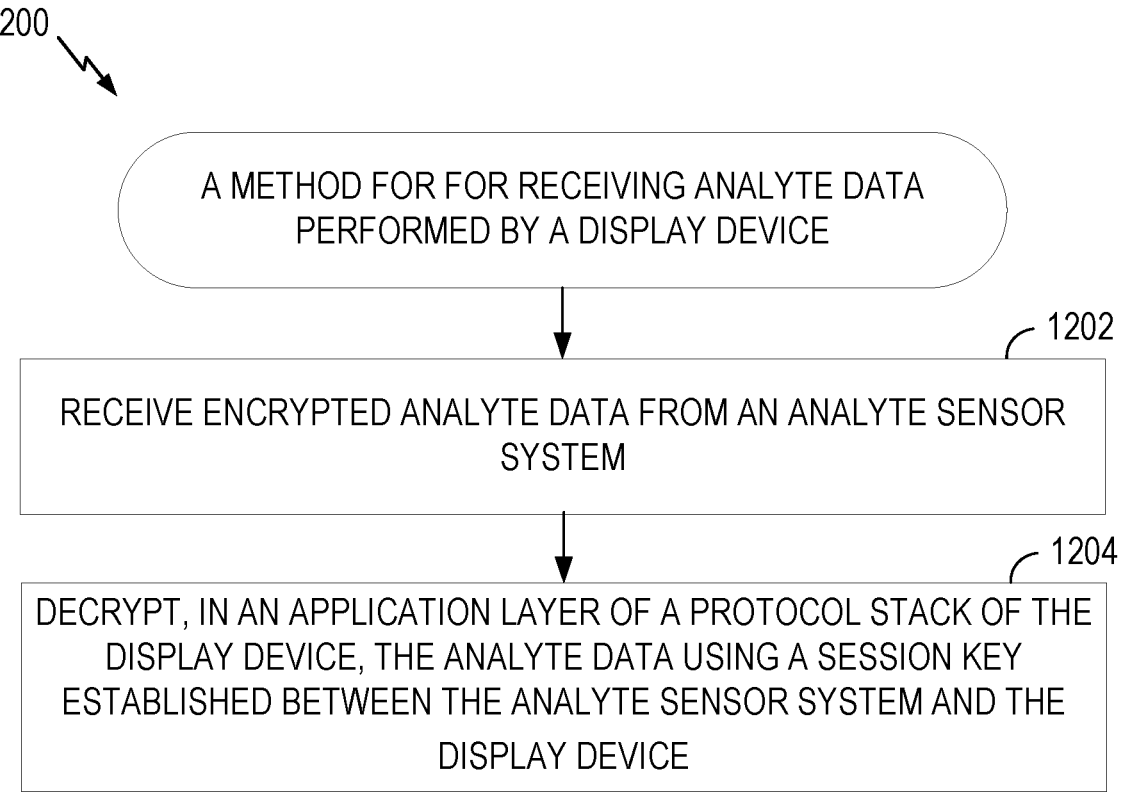
FIG. 12 is a flow diagram illustrating example operations for receiving analyte data performed by a display device, according to certain embodiments disclosed herein.

FIG. 12 is a flow diagram illustrating example operations 1200 for receiving analyte data of a user (e.g., a patient), according to certain embodiments described herein. The operations 1200 may be performed by one or more components of a display device, such as the one or more processors 126, the one or more memories 127, and/or the transceiver 129 of the display device 150. Additionally, it should be appreciated that operations 1200 are representative of the operations performed by the display device 150 described with respect to the ALE setup procedure 300 of FIG. 3 and the ALE setup procedure 600 of FIG. 6.

Operations 1200 begin in step 1202 with the display device receiving encrypted analyte data from an analyte sensor system.

In step 1204, the display device decrypts, in an application layer of a protocol stack of the display device, the analyte data using a session key established between the analyte sensor system and the display device.

In some embodiments, operations 1200 further include establishing a shared secret with the analyte sensor system. In some embodiments, establishing the shared secret with the display device is based on a juggling password authenticated key exchange using elliptic curve cryptography (EC-JPAKE) protocol.

In some embodiments, operations 1200 further include generating a first challenge message based on an authentication key derived from the shared secret. In some embodiments, operations 1200 further include transmitting the first challenge message to the analyte sensor system. In some embodiments, operations 1200 further include receiving, from the analyte sensor system, a first challenge response message and a second challenge message.

In some embodiments, operations 1200 further include generating a second challenge response message based, at least in part, on an authentication key derived from the shared secret and the first challenge message. In some embodiments, operations 1200 further include verifying that the first challenge response message received from the analyte sensor system matches the second challenge response message generated by the display device.

In some embodiments, operations 1200 further include generating a data protection key (DPK) and a device identification key (DIK). In some embodiments, the DPK and DIK are generated based, at least in part, on the shared secret, the first challenge message, and the second challenge message.

In some embodiments, operations 1200 further include generating an intermediate password authenticated key exchange key (PAKEkey) based, at least in part, on the shared secret, the first challenge message, and the second challenge message. In some embodiments, the DPK and DIK are generated based on a public key infrastructure (PKI) private key of the display device, a PKI public key of the analyte sensor system, and the intermediate PAKEkey.

In some embodiments, operations 1200 further include generating, based on the verifying, a third challenge response message based, at least in part, on the authentication key and the second challenge message. In some embodiments, operations 1200 further include transmitting the third challenge response message to the analyte sensor system. In some embodiments, operations 1200 further include receiving, based on the third challenge response message, an authentication completion message from the analyte sensor system.

In some embodiments, operations 1200 further include generating a first identification field based on the DIK and a first random number. In some embodiments, operations 1200 further include transmitting the first identification field and the first random number to the analyte sensor system. In some embodiments, operations 1200 further include receiving, based on the first identification field and the first random number, a second identification field and a second random number from the analyte sensor system. In some embodiments, operations 1200 further include generating a third identification field based on the DIK and the second random number. In some embodiments, operations 1200 further include verifying that the second identification field received from the analyte sensor system matches the third identification field generated by the display device.

In some embodiments, the first identification field, the second identification field, and the third identification field are padded based on a cryptography standard.

In some embodiments, operations 1200 further include generating, based on the verifying, the session key and a nonce based on the DPK, the first random number, and the second random number.

In some embodiments, the encrypted analyte data is encrypted twice based on the session key and a protocol-specific security key. In some embodiments, operations 1200 further include decrypting, in a lower layer of the protocol stack of the display device, the encrypted analyte data using the protocol-specific security key established between the analyte sensor system and the display device to obtain application layer encryption (ALE)-encrypted analyte data. In some embodiments, decrypting the encrypted analyte data in step 1204 comprises decrypting the ALE-encrypted analyte data using the session key.

EXAMPLE CLAUSES

Implementation examples are described in the following numbered clauses:

Clause 1: A computer-implemented method for transmitting analyte data performed by a sensor electronics module of an analyte sensor system, comprising: obtaining the analyte data from an analyte sensor operatively coupled to the sensor electronics module; encrypting, in an application layer of a protocol stack of the sensor electronics module, the analyte data using a session key established between the analyte sensor system and a display device; and transmitting the encrypted analyte data to the display device.

Clause 2: The computer-implemented method of Clause 1, further comprising establishing a shared secret with the display device.

Clause 3: The computer-implemented method of Clause 2, wherein establishing the shared secret with the display device is based on a juggling password authenticated key exchange using elliptic curve cryptography (EC-JPAKE) protocol.

Clause 4: The computer-implemented method of any of Clauses 2-3, further comprising: receiving a first challenge message from the display device; generating a second challenge message based, at least in part, on an authentication key derived from the shared secret; generating a first challenge response message based, at least in part, on the authentication key and the first challenge message; and transmitting the first challenge response message and the second challenge message to the display device.

Clause 5: The computer-implemented method of Clause 4, further comprising generating a data protection key (DPK) and a device identification key (DIK).

Clause 6: The computer-implemented method of Clause 5, wherein the DPK and the DIK are generated based, at least in part, on the shared secret, the first challenge message, and the second challenge message.

Clause 7: The computer-implemented method of Clause 5, further comprising generating an intermediate password authenticated key exchange key (PAKEkey) based, at least in part, on the shared secret, the first challenge message, and the second challenge message.

Clause 8: The computer-implemented method of Clause 7, wherein the DPK and DIK are generated based on a public key infrastructure (PKI) private key of the analyte sensor system, a PKI public key of the display device, and the intermediate PAKEkey.

Clause 9: The computer-implemented method of any one of Clauses 5-8, further comprising: receiving, from the display device, a second challenge response message; generating a third challenge response message based, at least in part, on the authentication key and the second challenge message; verifying that the second challenge response message received from the display device matches the third challenge response message generated by the sensor electronics module; and transmitting, based on the verifying, an authentication completion message to the display device.

Clause 10: The computer-implemented method of Clause 9, further comprising: maintaining a list of device identification keys (DIKs) and corresponding data protection keys (DPKs) associated with one or more display devices; receiving a first identification field and a first random number from a display device of the one or more display devices; selecting, from the list of DIKs, a DIK associated with the display device; generating a second identification field based on the selected DIK associated with the display device and the random number received form the display device; and verifying that the first identification field received from the display device matches the second identification field generated by the sensor electronics module.

Clause 11: The computer-implemented method of Clause 10, wherein the first identification field and the second identification field are padded based on a cryptography standard.

Clause 12: The computer-implemented method of any one of Clauses 10-11, further comprising: generating, based on the verifying, a second random number; generating a third identification field based on the selected DIK associated with the display device and a second random number; transmitting the third identification field and the second random number to the display device; and generating the session key and a nonce based on the first random number, the second random number, and a DPK corresponding to the selected DIK associated with the display device.

Clause 13: The computer-implemented method of Clause 12, wherein the third identification field is padded based on a cryptography standard.

Clause 14: The computer-implemented method of any one of Clauses 1-13, further comprising: encrypting, in a lower layer of the protocol stack of the sensor electronics module, the encrypted analyte data using a protocol-specific security key established between the analyte sensor system and the display device to obtain two-level encrypted analyte data, wherein transmitting the encrypted analyte data to the display device comprises transmitting the two-level encrypted analyte data to the display device.

Clause 15: A computer-implemented method for communicating analyte data performed by a display device, comprising: receiving encrypted analyte data from an analyte sensor system; and decrypting, in an application layer of a protocol stack of the display device, the encrypted analyte data using a session key established between the analyte sensor system and the display device.

Clause 16: The computer-implemented method of Clause 15, further comprising establishing a shared secret with the analyte sensor system.

Clause 17: The computer-implemented method of Clause 16, wherein establishing the shared secret with the display device is based on a juggling password authenticated key exchange using elliptic curve cryptography (EC-JPAKE) protocol.

Clause 18: The computer-implemented method of any one of Clauses 16-17, further comprising: generating a first challenge message based on an authentication key derived from the shared secret; transmitting the first challenge message to the analyte sensor system; and receiving, from the analyte sensor system, a first challenge response message and a second challenge message.

Clause 19: The computer-implemented method of Clause 18, further comprising: generating a second challenge response message based, at least in part, on an authentication key derived from the shared secret and the first challenge message; and verifying that the first challenge response message received from the analyte sensor system matches the second challenge response message generated by the display device.

Clause 20: The computer-implemented method of Clause 19, further comprising generating a data protection key (DPK) and a device identification key (DIK).

Clause 21: The computer-implemented method of Clause 20, wherein the DPK and the DIK are generated based, at least in part, on the shared secret, the first challenge message, and the second challenge message.

Clause 22: The computer-implemented method of Clause 20, further comprising generating an intermediate password authenticated key exchange key (PAKEkey) based, at least in part, on the shared secret, the first challenge message, and the second challenge message.

Clause 23: The computer-implemented method of Clause 22, wherein the DPK and DIK are generated based on a public key infrastructure (PKI) private key of the display device, a PKI public key of the analyte sensor system, and the intermediate PAKEkey.

Clause 24: The computer-implemented method of any one of Clauses 20-23, further comprising: generating, based on the verifying, a third challenge response message based, at least in part, on the authentication key and the second challenge message; transmitting the third challenge response message to the analyte sensor system; and receiving, based on the third challenge response message, an authentication completion message from the analyte sensor system.

Clause 25: The computer-implemented method of Clause 24, further comprising: generating a first identification field based on the DIK and a first random number; transmitting the first identification field and the first random number to the analyte sensor system; receiving, based on the first identification field and the first random number, a second identification field and a second random number from the analyte sensor system; generating a third identification field based on the DIK and the second random number; and verifying that the second identification field received from the analyte sensor system matches the third identification field generated by the display device.

Clause 26: The computer-implemented method of Clause 25, wherein the first identification field, the second identification field, and the third identification field are padded based on a cryptography standard.

Clause 27: The computer-implemented method of any one of Clauses 25-26, further comprising generating, based on the verifying, the session key and a nonce based on the DPK, the first random number, and the second random number.

Clause 28: The computer-implemented method of any one of Clauses 15-27, wherein the encrypted analyte data is encrypted twice based on the session key and a protocol-specific security key.

Clause 29: The computer-implemented method of Clause 28, further comprising: decrypting, in a lower layer of the protocol stack of the display device, the encrypted analyte data using the protocol-specific security key established between the analyte sensor system and the display device to obtain application layer encryption (ALE)-encrypted analyte data, wherein decrypting the encrypted analyte data comprises decrypting the ALE-encrypted analyte data using the session key.

Clause 30: An apparatus, comprising: one or more processors configured to execute instructions stored on one or more memories and to cause the apparatus to perform a method in accordance with any one of Clauses 1-29.

Clause 31: An apparatus, comprising means for performing a method in accordance with any one of Clauses 1-29.

Clause 32: A non-transitory computer-readable medium comprising executable instructions that, when executed by a processor of an apparatus, cause the apparatus to perform a method in accordance with any one of Clauses 1-29.

ADDITIONAL CONSIDERATIONS

Each of these non-limiting examples can stand on its own or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computer-implemented method for transmitting analyte data performed by a sensor electronics module of an analyte sensor system, comprising:
establishing a shared secret with a display device;
receiving a first challenge message from the display device;
generating a second challenge message based, at least in part, on an authentication key derived from the shared secret;
generating a first challenge response message based, at least in part, on the authentication key and the first challenge message;
transmitting the first challenge response message and the second challenge message to the display device;
obtaining the analyte data from an analyte sensor operatively coupled to the sensor electronics module;
encrypting, in an application layer of a protocol stack of the sensor electronics module, the analyte data using a session key established between the analyte sensor system and the display device based, at least in part, on the shared secret, the first challenge message, and the second challenge message; and
transmitting the encrypted analyte data to the display device.

2. The computer-implemented method of claim 1, wherein establishing the shared secret with the display device is based on a juggling password authenticated key exchange using elliptic curve cryptography (EC-JPAKE) protocol.

3. The computer-implemented method of claim 1, further comprising generating a data protection key (DPK) and a device identification key (DIK).

4. The computer-implemented method of claim 3, wherein the DPK and the DIK are generated based, at least in part, on the shared secret, the first challenge message, and the second challenge message.

5. The computer-implemented method of claim 3, further comprising generating an intermediate password authenticated key exchange key (PAKEkey) based, at least in part, on the shared secret, the first challenge message, and the second challenge message.

6. The computer-implemented method of claim 5, wherein the DPK and DIK are generated based on a public key infrastructure (PKI) private key of the analyte sensor system, a PKI public key of the display device, and the intermediate PAKEkey.

7. The computer-implemented method of claim 3, further comprising:

receiving, from the display device, a second challenge response message;

generating a third challenge response message based, at least in part, on the authentication key and the second challenge message;

verifying that the second challenge response message received from the display device matches the third challenge response message generated by the sensor electronics module; and transmitting, based on the verifying, an authentication completion message to the display device.

8. The computer-implemented method of claim 7, further comprising:

maintaining a list of device identification keys (DIKs) and corresponding data protection keys (DPKs) associated with one or more display devices;

receiving a first identification field and a first random number from a display device of the one or more display devices;

selecting, from the list of DIKs, a DIK associated with the display device;

generating a second identification field based on the selected DIK associated with the display device and the first random number received form the display device; and verifying that the first identification field received from the display device matches the second identification field generated by the sensor electronics module.

9. The computer-implemented method of claim 8, wherein the first identification field and the second identification field are padded based on a cryptography standard.

10. The computer-implemented method of claim 8, further comprising:

generating, based on the verifying, a second random number;

generating a third identification field based on the selected DIK associated with the display device and a second random number;

transmitting the third identification field and the second random number to the display device; and generating the session key and a nonce based on the first random number, the second random number, and a DPK corresponding to the selected DIK associated with the display device.

11. The computer-implemented method of claim 10, wherein the third identification field is padded based on a cryptography standard.

12. The computer-implemented method of claim 1, further comprising:

encrypting, in a lower layer of the protocol stack of the sensor electronics module, the encrypted analyte data using a protocol-specific security key established between the analyte sensor system and the display device to obtain two-level encrypted analyte data, wherein transmitting the encrypted analyte data to the display device comprises transmitting the two-level encrypted analyte data to the display device.

13. A computer-implemented method for communicating analyte data performed by a display device, comprising:

establishing a shared secret with an analyte sensor system;

generating a first challenge message based on an authentication key derived from the shared secret;

transmitting the first challenge message to the analyte sensor system;

receiving, from the analyte sensor system, a first challenge response message and a second challenge message;

receiving encrypted analyte data from the analyte sensor system; and decrypting, in an application layer of a protocol stack of the display device, the encrypted analyte data using a session key established between the analyte sensor system and the display device based, at least in part, on the shared secret, the first challenge message, and the second challenge message.

14. The computer-implemented method of claim 13, wherein establishing the shared secret with the display device is based on a juggling password authenticated key exchange using elliptic curve cryptography (EC-JPAKE) protocol.

15. The computer-implemented method of claim 13, further comprising:

generating a second challenge response message based, at least in part, on an authentication key derived from the shared secret and the first challenge message; and verifying that the first challenge response message received from the analyte sensor system matches the second challenge response message generated by the display device.

16. The computer-implemented method of claim 15, further comprising generating a data protection key (DPK) and a device identification key (DIK).

17. The computer-implemented method of claim 16, further comprising:

generating, based on the verifying, a third challenge response message based, at least in part, on the authentication key and the second challenge message;

transmitting the third challenge response message to the analyte sensor system; and receiving, based on the third challenge response message, an authentication completion message from the analyte sensor system.

18. The computer-implemented method of claim 17, further comprising:

generating a first identification field based on the DIK and a first random number;

transmitting the first identification field and the first random number to the analyte sensor system;

receiving, based on the first identification field and the first random number, a second identification field and a second random number from the analyte sensor system;

generating a third identification field based on the DIK and the second random number; and verifying that the second identification field received from the analyte sensor system matches the third identification field generated by the display device.

19. The computer-implemented method claim 18, further comprising generating, based on the verifying, the session key and a nonce based on the DPK, the first random number, and the second random number.

20. The computer-implemented method of claim 13, wherein:

the encrypted analyte data is encrypted twice based on the session key and a protocol-specific security key; and the computer-implemented method further comprises decrypting, in a lower layer of the protocol stack of the display device, the encrypted analyte data using the protocol-specific security key established between the analyte sensor system and the display device to obtain application layer encryption (ALE)-encrypted analyte data, wherein decrypting the encrypted analyte data comprises decrypting the ALE-encrypted analyte data using the session key.

\* \* \* \* \*